(12) United States Patent
Li et al.

(10) Patent No.: US 11,331,076 B2
(45) Date of Patent: May 17, 2022

(54) METHOD AND SYSTEM FOR DISPLAYING ULTRASONIC ELASTIC MEASUREMENT

(71) Applicant: Shenzhen Mindray Bio-Medical Electronics Co., Ltd., Shenzhen (CN)

(72) Inventors: Shuangshuang Li, Shenzhen (CN); Bo Wen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 680 days.

(21) Appl. No.: 16/252,095

(22) Filed: Jan. 18, 2019

(65) Prior Publication Data

US 2019/0254629 A1    Aug. 22, 2019

Related U.S. Application Data

(63) Continuation of application No. PCT/CN2016/092706, filed on Aug. 1, 2016.

(51) Int. Cl.
| | |
|---|---|
| *A61B 8/00* | (2006.01) |
| *A61B 8/14* | (2006.01) |
| *A61B 8/08* | (2006.01) |
| *G06T 11/20* | (2006.01) |
| *G01N 29/14* | (2006.01) |

(52) U.S. Cl.
CPC .............. *A61B 8/463* (2013.01); *A61B 8/08* (2013.01); *A61B 8/14* (2013.01); *A61B 8/485* (2013.01); *G01N 29/14* (2013.01); *G06T 11/206* (2013.01); *G06T 2200/24* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 2003/0028401 A1* | 2/2003 | Kaufman | G06Q 10/10 705/3 |
| 2003/0171676 A1 | 9/2003 | Trahey et al. | |
| 2004/0116808 A1* | 6/2004 | Fritz | A61B 8/467 600/437 |
| 2006/0241465 A1* | 10/2006 | Huennekens | A61B 5/06 600/458 |
| 2008/0071174 A1* | 3/2008 | Waki | A61B 8/485 600/442 |

(Continued)

FOREIGN PATENT DOCUMENTS

| | | |
|---|---|---|
| CN | 1658799 A | 8/2005 |
| CN | 101065067 A | 10/2007 |

(Continued)

*Primary Examiner* — Yi-Shan Yang
(74) *Attorney, Agent, or Firm* — Kory D. Christensen

(57) ABSTRACT

A probe generates a shear wave inside a target tissue, and allows the sear wave to pass through regions of interest sending a tracking pulse to the regions of interest through which the shear wave passes. A receiving circuit and beamforming unit receive echo information of the tracking pulse. A elasticity related result calculation unit calculates shear wave parameters according to the echo information of the tracking pulse, so as to obtain a corresponding elastic measurement result of the regions of interest and a corresponding relationship between the elastic measurement result and statistical variables and generates graphic marks.

16 Claims, 11 Drawing Sheets

(56) References Cited

U.S. PATENT DOCUMENTS

2012/0253194 A1* 10/2012 Tamura ............... G01S 7/52071
                                                                 600/438
2017/0119352 A1* 5/2017 Anand ................... A61B 8/465

FOREIGN PATENT DOCUMENTS

| CN | 101291629 | A | 10/2008 |
| CN | 101317774 | A | 12/2008 |
| CN | 102667522 | A | 9/2012 |
| CN | 103458800 | A | 12/2013 |
| CN | 103845074 | A | 6/2014 |
| CN | 104622509 | A | 5/2015 |
| CN | 104684488 | A | 6/2015 |
| CN | 105392428 | A | 3/2016 |
| JP | H08308831 | A | 11/1996 |
| JP | 2005218713 | A | 8/2005 |
| JP | 2007050065 | A | 3/2007 |
| JP | 2014140631 | A | 8/2014 |
| JP | 2015013099 | A | 1/2015 |
| JP | 2015146938 | A | 8/2015 |

* cited by examiner

METHOD AND SYSTEM FOR DISPLAYING ULTRASONIC ELASTIC MEASUREMENT

CROSS-REFERENCE TO RELATED APPLICATIONS

This application is a continuation of PCT Application No. PCT/CN2016/092706, filed Aug. 1, 2016, for "METHOD AND SYSTEM FOR DISPLAYING ULTRASONIC ELASTIC MEASUREMENT," which is incorporated herein by reference.

TECHNICAL FILED

The present disclosure relates to ultrasound elastography, and particularly to ultrasound elastography using shear waves and a measurement display method and system thereof.

BACKGROUND

Ultrasound elastography is one of the hotspots of clinical research in recent years. It mainly reflects the elasticity or softness of tissue, and is used more and more in auxiliary detection, benign and malignant discrimination and evaluation of prognosis of cancerous lesions, etc.

Ultrasound elastography mainly reflects the softness and hardness of tissue by imaging the elasticity-related parameters in a region of interest. In the past two decades, there have been many different methods for elastography, such as quasi-static elastography based on strain caused by a probe pressing the tissue, elastography or elastic measurement based on shear waves generated by acoustic radiation force, and instantaneous elastography based on shear waves generated by external vibration, etc. Among them, elastography or measurement technology based on shear waves has been widely concerned and welcomed by doctors since it can provide quantitative elastic indicators.

However, because the current shear wave elastography technology is susceptible to interference from patient breathing, heartbeat, vascular pulsation and probe movement, etc., the repeatability and stability of the measurement are relatively poor, which brings certain problems to the doctor's diagnosis. Therefore, it is desired to improve the measurement display of the shear wave elastography.

SUMMARY

The present disclosure provides a new method for displaying an ultrasound elastic measurement, which can provide a doctor with elastic measurement statistical analysis data as a diagnostic reference. The display of the elastic measurement result is more intuitive and more informative.

In one embodiment, an elastic ultrasonic measurement display method is provided. The method may include: generating a shear wave inside a target tissue which passes through a region of interest; transmitting a tracking pulse to the region of interest through which the shear wave passes, and receiving an echo information of the tracking pulse; calculating a shear wave parameter according to the echo information of the tracking pulse to obtain an elastic measurement result corresponding to the region of interest; obtaining a correspondence relationship between the elastic measurement result and a statistical variable; generating a graphic mark, wherein an attribute of the graphic mark is determined by the elastic measurement result; and displaying a relationship between the graphic mark and the statistical variable on a display to form an elastic statistical prompt chart associated with the region of interest.

In one embodiment, an elastic ultrasonic measurement display method is provided. The method may include: generating a first shear wave inside a target tissue; transmitting at least one tracking pulse to a region of interest through which the first shear wave passes, and receiving an echo information of the tracking pulse to obtain a first group of echo information; calculating a shear wave parameter according to the first group of echo information to obtain a first group of elastic measurement results; generating a first group of graphic marks, wherein an attribute of the first group of graphic marks is determined by the first group of elastic measurement results; and displaying the first group of graphic marks in an elastic statistical prompt chart window.

In one embodiment, an elastic ultrasonic measurement display system is provided. The system may include: a probe which generates a shear way inside a target tissue passing through a region of interest and transmitting a tracking pulse to the region of interest through which the shear wave passes; a receiving circuit and a beam-forming unit which receive an echo information of the tracking pulse; an elastic result calculation unit which calculates a shear wave parameter according to the echo information of the tracking pulse to obtain an elastic measurement result corresponding to the region of interest, obtains a correspondence relationship between the elastic measurement result and a statistical variable and generates a graphic mark, wherein an attribute of the graphic mark is determined by the elastic measurement result; and a display which displays a relationship between the graphic mark and the statistical variable to form an elastic statistical prompt chart associated with the region of interest.

In one embodiment, an elastic ultrasonic measurement display system is provided. The system may include: a probe which generates a first shear wave inside a target tissue and transmits at least one tracking pulse to a region of interest through which the first shear wave passes; a receiving circuit and a beam-forming unit which receives an echo information of the tracking pulse to obtain a first group of echo information; an elastic result calculation unit which calculates a shear wave parameter according to the first group of echo information to obtain a first group of elastic measurement results and generates a first group of graphic marks, wherein an attribute of the first group of graphic marks is determined by the first group of elastic measurement results; and a display which displays the first group of graphic marks in an elastic statistical prompt chart window

BRIEF DESCRIPTION OF THE DRAWINGS

In order to illustrate the embodiments of the present disclosure or the technical solutions in the prior art more clearly, the drawings used in the embodiments or the description of the prior art will be briefly described below. Obviously, the drawings in the following description are only certain embodiments of the present disclosure, and other drawings can be obtained by those skilled in the art according to these drawings without any creative work.

DETAILED DESCRIPTION

The technical solutions of the embodiments of the present disclosure will be clearly and completely described in the following with reference to the drawings of the embodiments of the present disclosure. It is obvious that the described embodiments are only a part, but not all, of the embodiments of the present disclosure. All other embodiments obtained by those skilled in the art based on the embodiments of the present disclosure without creative efforts will be within the scope of the present disclosure.

The present disclosure is based on shear wave ultrasonic imaging technology, and reflects the difference in hardness between tissues mainly by generating shear wave propagating inside the tissue and detecting and imaging its propagation parameters. Such methods have good stability and repeatability. In embodiments of the present disclosure, a method and system for measuring, counting and displaying tissue hardness may be provided. When a user collects and measures tissue elasticity, a special statistical prompt chart map may be used to display statistical analysis results of the elastic measurements and exhibits the distribution statistics of the elastic measurements over time variable and/or position variable. The time variable may represent any parameter that changes due to time changes or changes with time, such as the number of times of performing measurement by shear waves, the acquisition time of the shear wave parameters, the number of frames, and the system time, etc. The position variable may represent the coordinate position of an image pixel or image area. With the methods of the embodiments of the present disclosure, the stability and repeatability of each measurement can be intuitively presented during the process of collecting the elastic results by the user, which can not only help the user to easily eliminate abnormal measurement results, but also automatically perform statistical calculation for the results of multiple measurements, thereby improving the accuracy of the final measurement.

Figure 1:
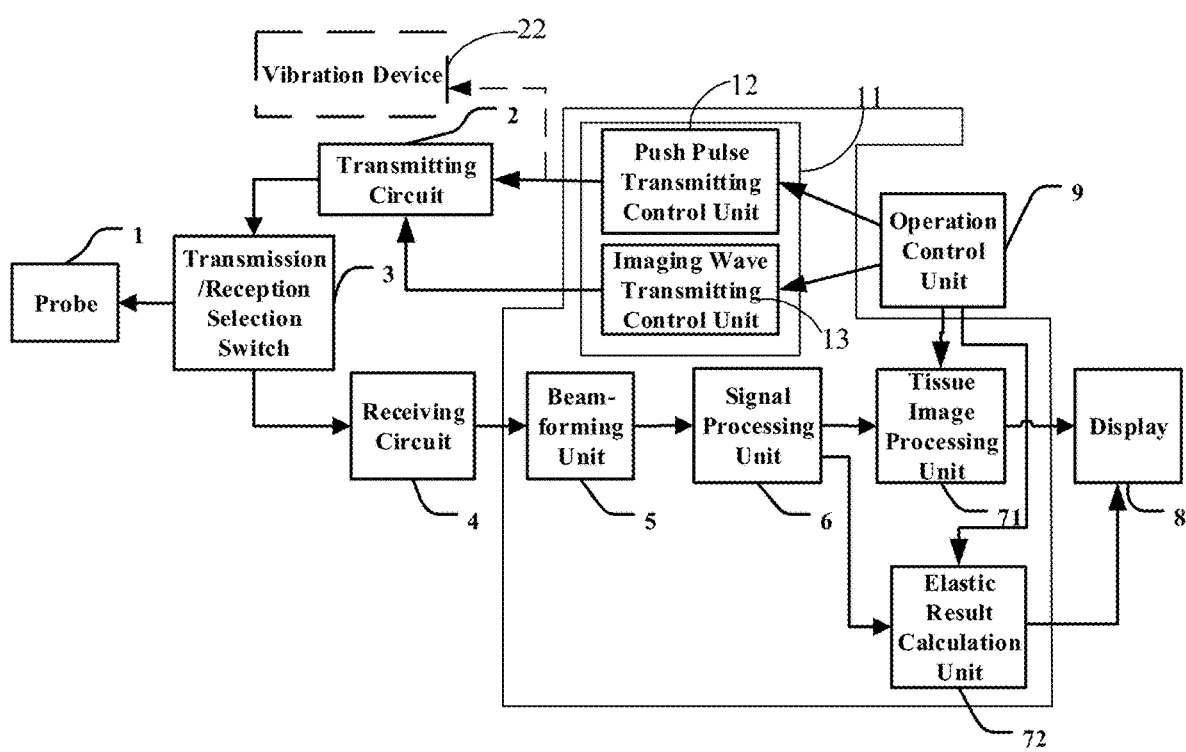
FIG. 1 is a schematic structural view of an ultrasound imaging system of the present disclosure.

FIG. 1 is a schematic structural diagram of an ultrasound imaging system of one embodiment of the present disclosure. The ultrasound imaging system may include a probe 1, a transmitting circuit 2, a transmission/reception selection switch 3, a receiving circuit 4, a beam-forming unit 5, a signal processing unit 6, a tissue image processing unit 71, an imaging wave transmitting control unit 13, and a display 8.

The imaging wave transmitting control unit 13 may generate an imaging wave transmitting sequence, and control the transmitting circuit 2 to transmit a delayed-focused transmission pulse with certain amplitude and polarity to the probe 1 through the transmission/reception selection switch 3. The probe 1 may be excited by the transmission pulse to transmit an ultrasound beam to a target tissue (e.g., an organ, a tissue, a blood vessel or the like in a human body or an animal body, not shown in the figures), and receive ultrasound echoes carrying information of the detected object reflected from the target tissue after a certain delay and convert the ultrasound echoes into electrical signals. The receiving circuit 4 may receive the electrical signals generated by the probe 1 to obtain ultrasound echo signals, and send the ultrasound echo signals to the beam-forming unit 5. The beam-forming unit 5 may perform processing such as focus delay, weighting and channel summation on the ultrasound echo signals, and then send the ultrasound echo signals to the signal processing unit 6 where related signal processing may be performed thereon. The ultrasound echo signals processed by the signal processing unit 6 may be sent to the image processing unit 71. The image processing unit 71 may perform different processing on the signals according to different imaging modes desired by the user to obtain ultrasound tissue image data of different modes. Then, ultrasound tissue images of different modes may be obtained by processing such as logarithmic compression, dynamic range adjustment and digital scan conversion, etc. The ultrasound tissue images may be displayed on the display 8. The ultrasound tissue images of different modes may include B images, C images, D images, etc., or other types of two-dimensional ultrasound tissue images or three-dimensional ultrasound tissue images.

In the tissue elastic ultrasound imaging process, the system of FIG. 1 may further include a push pulse transmitting control unit 12 and an elasticity result calculation unit 72. The push pulse transmitting control unit 12 may generate a push wave transmitting sequence to control the transmitting circuit 2 to transmit a delayed-focused transmission pulse with certain amplitude and polarity to the probe 1 through the transmission/reception selection switch 3 to generate a shear wave in the target tissue. The imaging wave transmitting sequence generated by the imaging wave transmitting control unit 13 may control the transmitting circuit 2 to transmit the transmission pulses to the probe 1 through the transmission/reception selection switch 3, and the probe 1 may be excited by the transmitting pulses to transmit tracking pulses to a region of interest in the target tissue through which the shear wave passes, and, after a certain delay, receive ultrasound echoes of the tracking pulses reflected from the region of interest in the target tissue and convert the ultrasound echoes into an electrical signals to obtain ultrasound echo signals. The receiving circuit 4 may receive the ultrasound echo signals and send the ultrasound echo signals to the beam-forming unit 5. And then, after processed by the signal processing unit 6, the ultrasound echo signals may be sent to the elasticity result calculation unit 72 where the shear wave parameters corresponding to the region of interest may be calculated to obtain the elasticity measurements corresponding to the region of interest. Furthermore, a statistical analysis may be performed on the elasticity measurements to obtain elasticity statistical results. The elasticity measurements and the elasticity statistical results may be sent to the display 8 and simultaneously displayed with the ultrasound tissue image.

In addition, the ultrasonic imaging system may further include an operation control unit 9 for receiving an adjustment signal inputted by the user. The adjustment signal may include an adjustment to the imaging parameter such as the push wave transmitting sequence, the imaging wave transmitting sequence, or the like, or may further include an adjustment to the image generated by the image processing unit, the region of interest or the calculation result of the elasticity result calculation unit. The operation control unit 9 may be a human-computer interaction interface, such as a keyboard, a scroll wheel, a touch screen with a touch function, a mouse, a transceiver unit for a gesture control signal, and the like.

The imaging wave transmitting control unit 13 and the push pulse transmitting control unit 12 may be integrated in one or more processors, and the imaging wave transmitting sequence and the push wave transmission sequence may be generated by the same processing unit in a time series or in accordance with a user input instruction. Of course, the beam-forming unit 5, the signal processing unit 6, the image processing unit 71, the elasticity result calculation unit 72, the imaging wave transmitting control unit 13 and the push pulse transmitting control unit 12 may be implemented in different processors or circuits to achieve different functions, or be integrated in one or more processors where software programming may be used to achieve the division of multiple functional units.

The system in FIG. 1 may be based on the principle of acoustic radiation force elastography. Furthermore, based on the vibration device shown in the dashed box 22 and the dashed arrows in FIG. 1, another tissue elastography system may be provided. In this embodiment, the push pulse transmitting control unit 12 may generate a push wave transmitting sequence which is supplied to the vibration device 22 for generating a mechanical vibration force. The mechanical vibration force may excite the target tissue to generate a shear wave therein. And then, with reference to the processes described above, the imaging wave transmitting control unit 13 may generate an imaging wave transmitting sequence to control the transmitting circuit 2 to cause the probe 1 to be excited by the transmitting pulses to transmit tracking pulses to the region of interest in the target tissue through which the shear wave passes and receive the echoes of the tracking pulses. The echo signals may be passed through and processed by the receiving circuit 4, the beam-forming unit 5, the signal processing unit 6 and the elasticity result calculation unit 72 to obtain the elastic statistical results, which may be sent to the display 8 to be displayed with the ultrasound tissue image.

Figure 2:
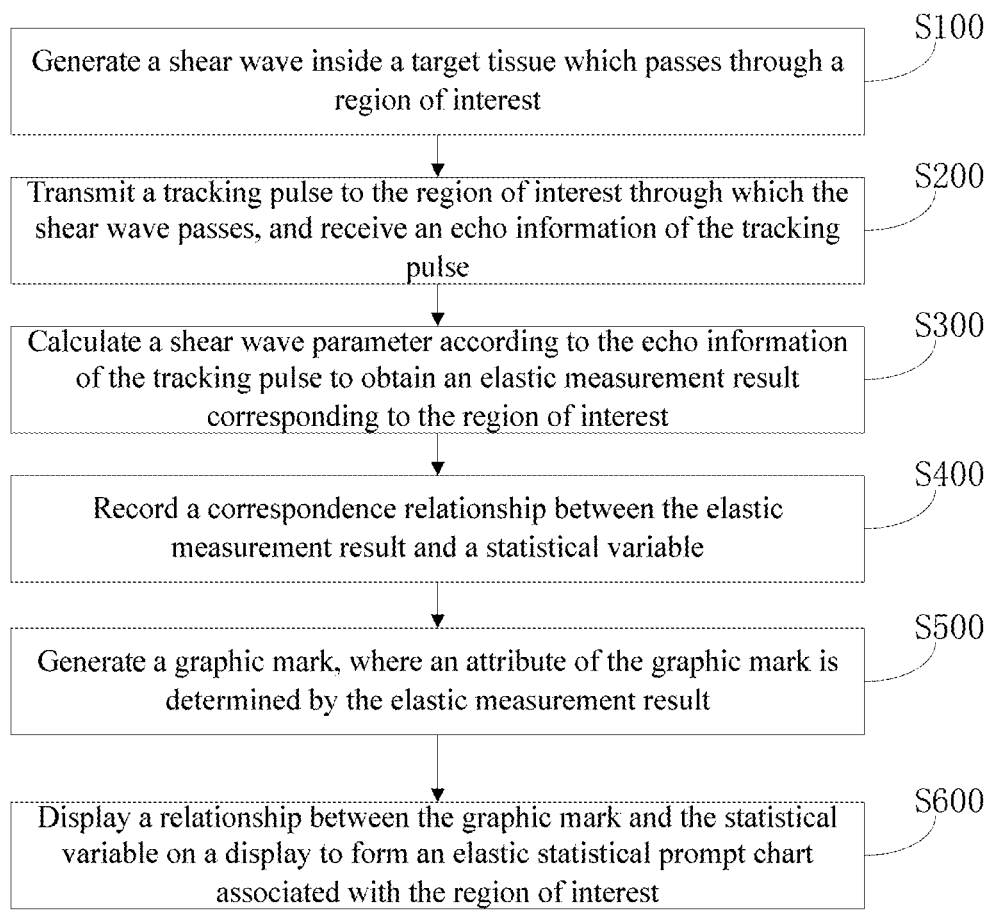
FIG. 2 is a schematic flow chart of one embodiment of an ultrasound elastic measurement display method of the present disclosure.

It can be seen that the elastic ultrasonic measurement display methods shown in figures such as FIG. 2, etc. of the present disclosure may be applicable for both the acoustic radiation force elastography system and the transient elastic imaging system.

FIG. 2 is a schematic flow chart of an ultrasound elastic measurement display method of one embodiment of the present disclosure;

In step S100, a shear wave may be generated inside the target tissue by the probe and passed through the region of interest.

Figure 3:
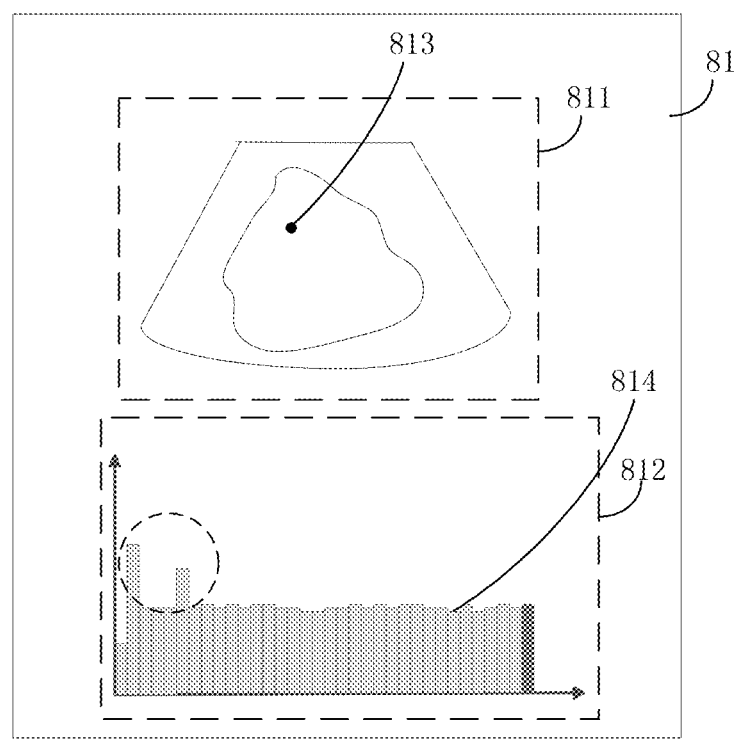
FIG. 3 is a resultant view of the method of FIG. 2 in one embodiment.

Before the step S100, based on the system in FIG. 1, ultrasound beams may be transmitted to the target tissue by the probe to obtain the ultrasound tissue image of the target tissue, as described with reference to FIG. 1. In the present embodiment, the ultrasound tissue image may be an ultrasound tissue image of different modes, such as a B image, a C image, a D image, or the like, or other types of two-dimensional ultrasound tissue images or three-dimensional ultrasound tissue images. As shown in FIG. 3, on the display interface 81 of the display 8, the ultrasound tissue image may be displayed in the ultrasound tissue image display area 811. The ultrasound tissue image display area 811 may be any area on the display interface 81. The ultrasound beams transmitted to the target tissue by the probe may be any one of plane wave beam, focused wave beam and divergent wave beam, etc., or a combination thereof.

The ultrasound tissue image may include real-time ultrasound tissue images acquired by the ultrasound imaging system, ultrasound tissue image video data acquired over a period of time by the ultrasound imaging system, or a certain frame of ultrasound tissue image acquired by the ultrasound imaging system, etc. The system shown in FIG. 1 may further include a storage device for storing the cached image data and the intermediate data generated during analysis and processing, such as a hard disk, a cache unit or the like.

Based on the obtained ultrasound tissue image, the image processing unit may identify the region of interest in the ultrasound tissue image, or obtain the region of interest based on the system default. The region of interest referred to herein may include one of: one pixel in the ultrasound tissue image, a multiple pixels distributed discretely in the ultrasound tissue image, a multiple pixels distributed continuously in the ultrasound tissue image, an image region representing the entire scan area of the probe, a multiple image regions distributed discretely and the like. As shown in FIG. 3, the region of interest 813 is a small pixel region or image region, and an elastic statistical prompt chart 812 obtained according to step S600 may be displayed below the ultrasound tissue image display region 811. The elastic statistical prompt chart 812 may include a multiple sets of graphic marks 814 which represent the statistical results of multiple elastic measurements continuously performing on the region of interest 813. The overall analysis results of the elastic measurement of the same region of interest can be obtained intuitively from FIG. 3, and it is easy to intuitively eliminate the two measurement results with too large errors in the dashed box in the figure, thereby providing more accurate measurement results to the user.

The region of interest may be obtained based on system defaults, based on user input inputted through the operation control unit and/or based on an image automatic segmentation processing methods. For example, based on the system default, an image region that represents the entire scan area of the probe or an image region that represents a part of the scan area of the probe and includes a multiple pixels distributed consecutively may be used as the region of interest.

For example, the region of interest may be determined based on a selection instruction inputted in the obtained ultrasound tissue image by the user using the operation control unit. The operation control unit herein may be a human-computer interaction device, such as a mouse, a keyboard, or a scroll wheel, etc. Alternatively, in the case that the display is a touch screen, the operation control unit may be a gesture detection unit for detecting a selection instruction given by the user on the touch screen. The region of interest in this embodiment may be one pixel, a multiple pixels distributed discretely or an image region consisting of a multiple pixels distributed continuously selected in the ultrasound tissue image, or may also be an image region representing the entire scan area of the probe.

For example, the identification of the region of interest may also be based on an automatic image segmentation processing method that is automatically operated by the system. For example, an image automatic segmentation processing may be performed on an obtained ultrasound heart image to identify an image region or a partial image region of an organ such as an arterial root vessel wall, a ventricular wall, or the like. The image region or partial image region of the organ obtained by the automatic image segmentation algorithm may be the region of interest in step S100.

Further, the identification of the region of interest may also be a semi-automatic process. For example, a region of organ of the target tissue (e.g., a heart wall, a liver, a stomach wall, a blood vessel wall, and the like) may be obtained based on an image automatic segmentation processing algorithm operated automatically by the system, and then the region of interest mentioned above may be determined according to a selection instruction inputted by the user in the region of organ of the target tissue through the operation control unit. For example, based on the system default, an image region representing the entire scan area of the probe or an image region that represents a part of the scan area of the probe and includes a multiple pixels distributed consecutively may be used as a target region, and then, the region of interest mentioned above may be determined according to a selection instruction inputted by the user in the target region through the operation control unit.

The region of interest obtained by the identification above may be used to determine a target position for performing tissue elasticity measurement using shear waves, and may also be used to determine a measurement position corresponding to the elastic measurement result. For example, when the tissue elasticity of the image region or partial image region (including a region consisting of a multiple pixels distributed continuously) representing the entire scan area of the probe is measured using the shear wave, the region of interest may be obtained based on a secondary positioning recognition. For example, in the image region or partial image region representing the entire scan area of the probe, a selection instruction inputted by the user may be received to obtain a corresponding region of interest. In step S300, the shear wave parameters in the entire image region or partial image region representing the entire scan area of the probe may be calculated, while when obtaining the elastic measurement results corresponding to the region of interest, the shear wave parameters corresponding to the region of interest obtained by the secondary positioning recognition may be obtained from the shear wave parameters calculated in whole and used to calculate the elastic measurement results.

Therefore, the identification of the above-mentioned region of interest may be identified manually, automatically or semi-automatically. In addition, there may be one or more regions of interest ("more" herein refers to two or more than two). In one embodiment of the present disclosure, the elastic statistical prompt charts corresponding to multiple regions of interest may also be obtained simultaneously based on the multiple regions of interest. In one embodiment of the present disclosure, the number of the region of interest may be determined by user selection or by system defaults. When there are multiple regions of interest, the user can simultaneously acquire the tissue elasticity parameters of the multiple regions of interest and observe them comparatively. The elastic statistical prompt charts that may be used to compare and observe the multiple regions of interest may be displayed.

Moreover, in one embodiment of the present disclosure, the number, orientation and size of the region of interest may be selected by the user. For example, the user can input an adjustment instruction about the number, orientation, and size of the region of interest through the operation control unit 9. The image processing unit may obtain the adjustment instruction to update the region of interest displayed on the display. In addition, according to the adjustment instruction, the graphic mark that has been displayed in step S600, that is, the graphic mark in the elastic statistical prompt chart, can be cleared, which is also be referred to as adjustment of the region of interest. The previous data may be cleared, and the graphic mark may be re-outputted.

In step S200, the probe may transmit tracking pulses to the region of interest through which the shear wave passes, and the receiving circuit and the beam-forming unit may receive the echo information of the tracking pulses. The shear wave may be generated in the ways described in detail above with reference to FIG. 1. The position at which the shear wave is generated may be determined according to the default setting of the system or according to the position of the region of interest.

In this step, various methods can be used to generate shear waves inside the tissue, such as generating the shear wave inside the tissue by external vibration external to the tissue, and generating the shear wave inside the tissue by transmitting acoustic radiation force impulses (ARFI) to the inside of the tissue. The acoustic radiation force impulse may or may not be focused. The tracking pulses may be any of plane wave beam, focused wave beam, divergent wave beam and the like, or a combination thereof.

It can be understood that since the shear wave generated by the acoustic radiation force pulse itself has small amplitude, and since the shear wave will be rapidly attenuated with the propagation, a series of acoustic radiation force pulses may be transmitted in order to increase the shear wave intensity, broaden the propagation range of the shear wave or change the characteristics of the shear wave waveform so as to improve the detection sensitivity, thereby avoiding the effects of the attenuation of the shear wave to the imaging.

Further, in one embodiment, multiple focused pulses may be successively transmitted to the same measurement position to increase the intensity of the generated shear wave. It is also possible to change the positions to which the focused pulses are transmitted successively in a longitudinal direction (the direction of the focused transmitting) or a lateral direction (the direction perpendicular to the focused transmitting) so as to broaden the propagation range of the shear wave and make the shear wave to propagate along a certain direction. Alternatively, the pulses may be simultaneously transmitted at different lateral positions such that two shear wave waveforms arriving at different times are superimposed so as to facilitate the detection.

For example, in one embodiment, step S200 may further include the following steps:

Step S210, estimating the propagation velocity of the shear wave in the target tissue.

After the shear wave is generated, it begins to propagate in the tissue. Its propagation velocity is different depending on the elastic properties of the tissue. In order to estimate and track the shear waves, an average velocity $\bar{c}$ and a possible velocity range $c_l$ to $c_h$ can be estimated according to the target tissue. The average velocity and the velocity range can be pre-specified by the system with reference to existing academic measurement data or measurement experience, etc. For example, the average propagation velocity of the shear wave in the target tissue may be specified to be about 2 m/s, and the possible velocity range be 1~4 m/s, etc. Alternatively, the average propagation velocity may be specified to be 1 m/s, and the possible velocity range be 0.5~2 m/s, etc.

Step S220, estimating the positions of the shear wave in the target tissue at different times according to the propagation velocity of the shear wave in the target tissue to obtain the estimated shear wave position of the shear wave at the times.

Assuming that the initial propagation time of the shear wave is $t_0$, at different times $t_k$ after the shear wave is generated, the distance $\overline{d}_k$ of the shear eave from the shear wave source can be estimated as:

$$\overline{d}_k = (t_k - t_0) * \overline{c}$$

Assuming that the time interval between two adjacent detection times is $\Delta t$, that is, $\Delta t = t_k - t_{k-1}$, the propagation range $\Delta d_l \sim \Delta d_h$ of the shear wave between the two detection times can be estimated as:

$$\Delta d_l = c_l \Delta t$$

$$\Delta d_h = c_h \Delta t$$

Therefore, the moving distance of the shear wave detecting position between two adjacent detection times is less than or equal to $\Delta d_l$ so as to avoid that the estimated position is advanced when the shear wave propagation is too slow. The detection width for the shear wave is greater than or equal to $\Delta d_h - \Delta d_l = \Delta t(c_h - c_l)$ in each detection, so as to ensure that the estimated position can contain all possible positions of the shear wave at that time.

Step S230, transmitting tracking pulses to the corresponding estimated shear wave positions at the times, and receiving echo information of the tracking pulses.

Figure 4:
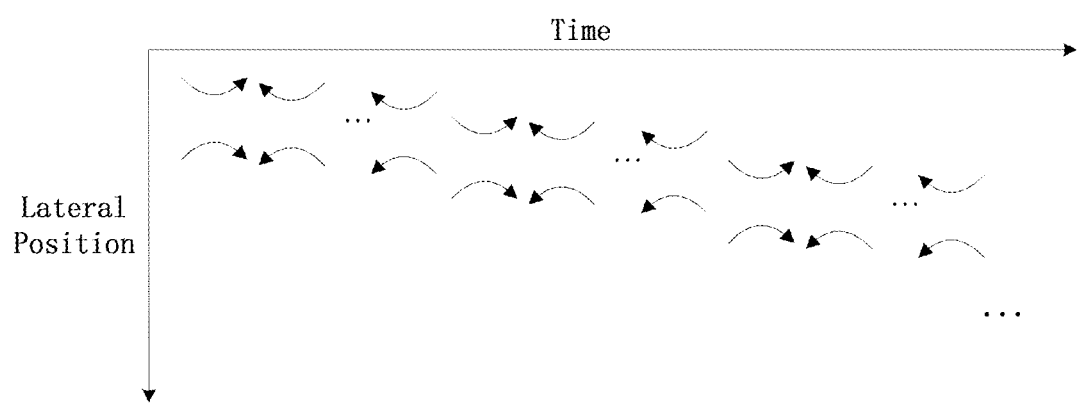
FIG. 4 is a schematic diagram of the transmission and reception of the tracking pulse during shear wave propagation.

As shown in FIG. 4, beginning from the start of the shear wave propagation, the system may transmit tracking pulses in an interval $\Delta t$ to perform continuous detection. In each detection, a certain detection lateral beam width may be maintained, that is, echo information in a certain width may be simultaneously acquired. The echo information may include the information of each of the lateral positions in the certain width above. The interval of the lateral positions may not be too large, so as to ensure a certain lateral resolution. At the same time, the distance between the centers of the beam of adjacent detection may be less than $\Delta d_l$. Alternatively, in the case that $\Delta t$ is small which cause that $\Delta d_l$ is too small, it is equivalent to that the distance between the center of the beam at every n detection times is less than $n\Delta d_l$. The system may start the detection from any time or start the detection from a position which is from the shear wave source in a certain distance. The possible position of the shear wave at the current position or the current time may be estimated according to the average propagation velocity, and after the shear wave propagates to this position and leave, the center position of the detection can be changed.

Since in each detection a certain lateral beam width is maintained and the lateral line spacing cannot be too large so as to ensure a certain lateral resolution, the system may have ultra-wide beam forming capability, that is, it can acquire echo information of multiple lateral positions at the same time. The number of beams may be, for example, 1 to 1024. It may be adjusted by the system as needed, such as 4 beams, 16 beams, 32 beams, 64 beams, 96 beams, 128 beams, and the like. The wider the beam, the weaker the focus of the transmitted sound field, and the more uniform and un-concentrated the lateral distribution of the sound field energy, which reduces the signal-to-noise ratio at each detection position in the beam. In order to improve the detection quality, for a same center position, the transmitting may be continuously performed for multiple times and each transmitting has different beam angle. And then, the echo signals of different angles may be combined to increase the signal-to-noise ratio. The number of the angles and the sizes of the steering angle may be adjusted by the system according to actual needs. For example, three steering angles may be used, such as −5°, 0° and 5°, etc.

In step S300, the elasticity result calculation unit may calculate the shear wave parameters according to the echo information of the tracking pulses to obtain the elastic measurement result corresponding to the region of interest. Various shear wave parameters may be calculated according to the echo information of the tracking pulse, such as shear wave propagation distance, shear wave propagation velocity, Young's modulus, shear modulus, and the like. The elastic measurement result corresponding to the region of interest may be a direct result of the calculation of the shear wave parameter, or a statistic of the parameters in the region of interest, e.g., maximum value, minimum value, mean, standard deviation, mean variance or grade score, etc. of the parameters in the region of interest.

In this step, the echo information of the tracking pulse at the times may be integrated to obtain the echo information of the shear wave in a short time period at various positions of the target tissue during the propagation of the shear wave, where the shear wave passes through the corresponding positions just in the short time period.

In one embodiment of the present disclosure, the step S300 may further include the following steps:

Step S301: obtaining reference information. It can be understood that the reference information can be selected according to needs. For example, the echo information of the tracking pulses at a certain time at the corresponding position may be selected as the reference information. It is also possible to transmit a reference pulse before the shear wave propagation and use the echo information of the reference pulse as reference echo information. The reference information may be used for cross-correlation comparison with the tracking pulses tracking the shear wave.

Step S302, performing cross-correlation comparison between the echo information of the tracking pulse at different times at the positions in the target region and the reference information corresponding to the positions to obtain the particle displacement data at different times at the positions. Further, a displacement-time curve at the position may be generated. During the time period, the shear wave experiences the entire process of approaching, reaching and leaving the position, with peaks appearing in the corresponding curves. Due to the estimated tracking detection, a corresponding small displacement-time curve can be obtained for each lateral position, where the times corresponding to the curves are different. The times corresponding to the adjacent positions may partially overlap. The position of the peak on the displacement-time curve corresponds to the moment when the shear wave reaches the position.

There are various methods for calculating the propagation velocity of the shear wave. For example, by performing cross-correlation comparison between the displacement-time curves corresponding to two different lateral positions at the same depth, the time difference between the two lateral positions can be obtained. Such time difference corresponds to the shear wave propagation time between these two lateral positions. The ratio of the distance between the lateral positions to the propagation time is the propagation velocity between the two lateral positions.

For example, for a certain position, the displacement data of the lateral positions corresponding to two times at which the shear wave reaches the positions may be taken out to form displacement-transverse position curves of the two times. The cross-correlation comparison may be performed on the two curves to obtain the difference in lateral position between the two times. This difference in lateral position corresponds to the propagation distance of the shear wave between the two times. The ratio of the propagation distance to the time difference between the two times is the propagation velocity near the position.

For example, the approximate calculation formula may be derived by directly using the wave propagation equation as follows:

$$c \approx \sqrt{\frac{\partial^2 u_z/\partial t^2}{\partial^2 u_z/\partial x^2 + \partial^2 u_z/\partial z^2}}$$

Where c is the propagation velocity, $u_z$ may be regarded as longitudinal displacement data, or may also be longitudinal velocity data, x represents the lateral coordinate, and z represents the longitudinal coordinate. It is also possible to transform the above formula into the frequency domain for calculation.

Under certain conditions, the propagation velocity of the shear wave has a nearly fixed relationship with the tissue hardness:

$E=3\rho c^2$

In this formula, $\rho$ represents the tissue density, and E represents the Young's modulus value of the tissue. Under certain conditions, the larger the Young's modulus, the greater the tissue hardness.

In addition, from the value of the propagation velocity of the shear wave at the positions, the shear modulus, the propagation distance in a certain fixed time period, the average propagation velocity in the target region, the Young's modulus and the like may be further calculated.

The elastic measurement results in this embodiment may be one of various measurements such as Young's modulus, shear modulus, shear wave velocity and shear wave propagation distance, etc. In the system of the present embodiment, the user can freely select the measurements for the elastic measurement results. For example, the user can input a change instruction for the measurement manner of the elastic measurement results by the operation control unit 9, and the elasticity result calculation unit may acquire the change instruction and update the graphic mark displayed on the display. The updated content may include the attribute of the graphic marks or coordinate system of the elastic statistical prompt chart on which the graphic marks are located, etc.

The process of the above steps S100 to S300 may include a measurement process of performing multiple shear wave transmissions using the probe. In one embodiment of the present disclosure, the probe may be used to generate multiple shear waves inside the target tissue and make them to pass through the region of interest respectively. The tracking pulses may be transmitted to the region of interest through which the multiple shear waves pass by the probe for multiple times, respectively. The receiving circuit and the beam-forming unit may respectively receive the echo information corresponding to the multiple tracking pulses to obtain multiple groups of echo information. The elasticity result calculation unit may calculate the parameters of the multiple shear waves according to the multiple groups of echo information to obtain multiple groups of elastic measurement results of the multiple measurements to the region of interest, respectively. The correspondence relationship between the multiple groups of elastic measurement results and the time variable may be obtained to generate multiple groups of graphic marks. Each group of elastic measurement results can determine the attributes of one group of graphic marks. The relationship between multiple groups of graphic marks and the time variables may be displayed on the display to form the elastic statistical prompt chart to display the results of the statistics analysis of the multiple shear wave measurements to the region of interest, as shown in FIG. 3.

The process of calculating the shear wave parameter according to the echo information of the tracking pulse in the step S300 above may be performed based on the system default initial range containing the region of interest. For example, in one embodiment of the present disclosure, based on the system defaults or the user's first input, the image region representing the entire scan area of the probe or the image region representing a part of the scan area of the probe and consisting of multiple pixels distributed continuously may be used as the target region. The target region may contain the region of interest. And then, the process of calculating the shear wave parameters in steps S100 to S300 above may be performed, as follows:

First, the probe may be used to generate a shear wave inside the target tissue which passes through the target region containing the region of interest;

Secondly, the probe may transmit tracking pulses to the target region through which the shear wave passes, and the receiving circuit and the beam-forming unit may receive the echo information of the tracking pulses;

Then, the elasticity result calculation unit may calculate the shear wave parameters according to the echo information of the tracking pulses to obtain elastic measurement results corresponding to the target region;

Finally, the elasticity result calculation unit may obtain the elastic measurement results corresponding to the region of interest from the elastic measurement results corresponding to the target region.

The target region above is not limited to the image region representing the entire scan area of the probe or the image region representing a part of the scan area of the probe and consisting of a multiple pixels distributed consecutively, but may also be any image region selected by the user on the ultrasound tissue image or an image region representing one or more biological tissue structures acquired by the system by running an automatic image segmentation processing method.

Before obtaining the elastic measurement results corresponding to the region of interest from the elastic measurement results corresponding to the target region, the method may further include identifying the region of interest from the ultrasound tissue image based on the user's selection or automatic recognition of the system.

When there are multiple regions of interest whose elastic measurement results need to be displayed, the image region in which the multiple regions of interest are located may be used as the target region to perform the shear wave measurement process to obtain the elastic measurement results of the target region, and then the elastic measurement results corresponding to the multiple regions of interest may be obtained from the elastic measurement results of the target region. Alternatively, the measurement process of the shear wave may be separately performed to the multiple regions of interest to sequentially obtain the elastic measurement results corresponding to the multiple regions of interest.

In step S400, the elasticity result calculation unit may obtain the correspondence relationship between the elastic measurement results and the statistical variable. The statistical variable may includes at least one of the position variable and the time variable.

The time variable may represent any parameter that changes due to time changes or changes with time, such as the number of the shear wave measurements performed, the acquisition time of the shear wave parameters, the number of frames, and the system time, etc.

The position variable may represent the coordinate position of the image pixel or image area in the ultrasound tissue image. For such position variable, it is possible that the coordinate position on one axis is fixed while the coordinate position on the other one or two axes are changed, the coordinate position is changed in the propagation direction of the ultrasound beam or the tracking beam, or the coordinate position is changed in the propagation direction of the shear wave. It may also be possible that the coordinate position is changed in any direction selected in the ultrasound tissue image.

When there are multiple regions of interest, the correspondence relationships between the elastic measurement results corresponding to the multiple regions of interest and the position variables may be obtained, so as to generate multiple graphic marks according to the elastic measurement results respectively corresponding to the multiple regions of interest. The graphic marks may be synchronously displayed in the elastic statistical prompt chart according to the spatial positional relationship of the position variable so as to comparatively show the elastic measurement results of the multiple regions of interest. The spatial positional relationship herein may include the spatial relationship of the coordinate positions of the multiple regions of interest in the ultrasound tissue image.

When there is one region of interest, the correspondence relationship between the elastic measurement results corresponding to this region of interest and the time variable may be obtained so as to generate multiple groups of graphic marks that vary with time variables. The corresponding graphic marks may be sequentially displayed in the elastic statistical prompt chart according to the order of change of the time variables so as to show the measurement results of the same position measured for multiple times one by one, thereby facilitating the doctor to make an overall evaluation and eliminate the measurement results with large errors.

When the two cases above are combined for multiple regions of interest, the correspondence relationship between the elastic measurement results corresponding to the multiple regions of interest and the position variable and the time variable may be obtained, so as to generate multiple groups of graphic marks which change with time variables. Each group of graphic marks may include multiple graphic marks generated according to the elastic measurement results respectively corresponding to the multiple regions of interest at the same time variable. The measurement results of the multiple regions of interest on which the tissue elasticity measurements are performed simultaneously may be comparatively shown in the elastic statistical prompt chart such that the user can continuously observe the changes of elastic parameters at certain positions in a certain region range and more clearly understand the distribution of the elasticity results in the entire region. In one embodiment of the present disclosure, the correspondence relationships between all of the elastic measurement results acquired in a time period and the statistical variables may be stored in the storage device. In one embodiment of the present disclosure, the correspondence relationship between all of the calculated shear wave parameters obtained in a time period and the statistical variables may be stored in the storage device, so as to facilitate the elasticity result calculation unit to obtain the elastic measurement results corresponding to the region of interest from the elastic measurement results corresponding to the target region to form the correspondence relationship between the elastic measurement results corresponding to the stored region of interest and the statistical variable.

Figure 14:
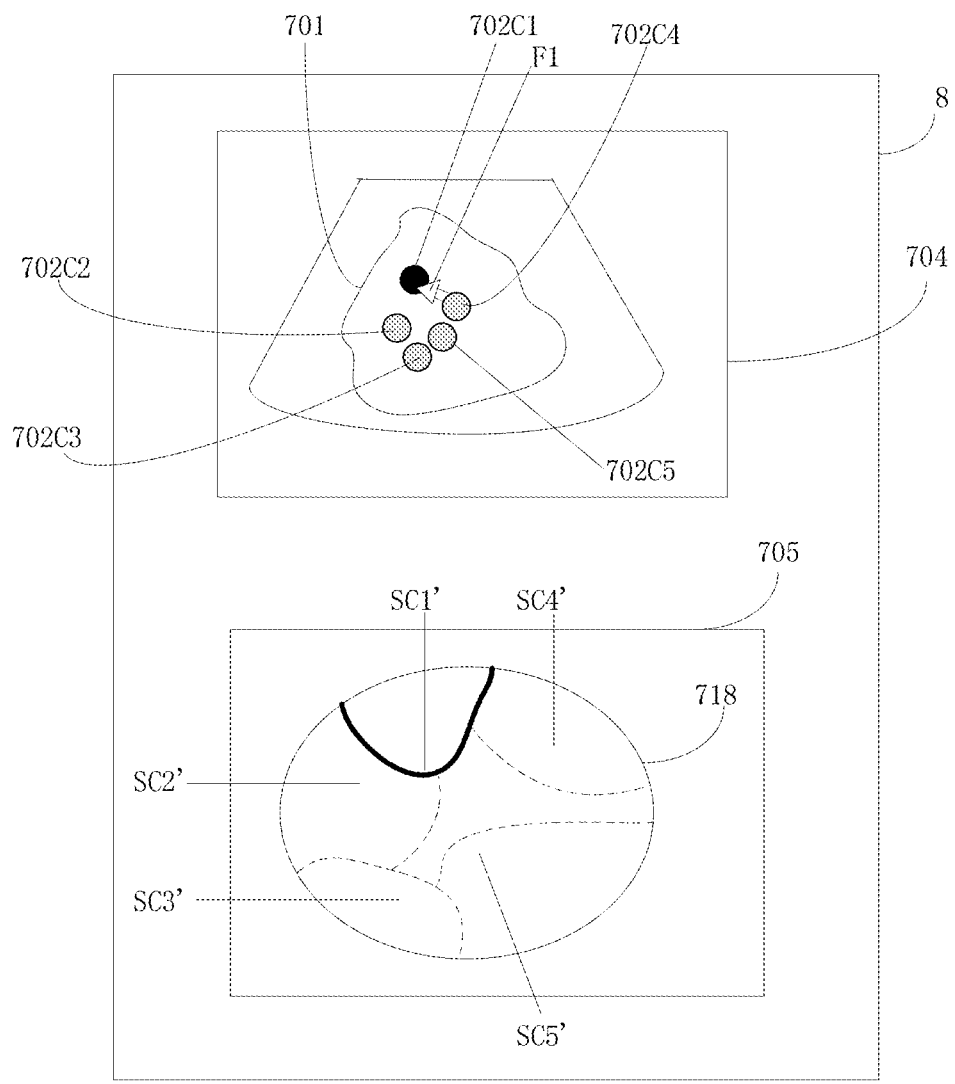
FIG. 14 is another resultant view with separate elastic statistical prompt chart window in the case that there are multiple regions of interest.

In step S500, the elasticity result calculation unit may generate the graphic marks whose attributes may be determined by the elastic measurement results above. Based on the change of the time variable, multiple groups of graphic marks may be sequentially generated, and based on the change of the coordinate positions of the multiple regions of interest, multiple graphic marks may be respectively generated. These graphic marks may be combined, that is, each group of graphic marks may include multiple graphic marks, as described above. The attributes of one group of graphic marks may be determined by the elastic measurement results corresponding to one time variable value, while the attributes of one graphic mark may be determined by the elastic measurement results corresponding to one region of interest. Similarly, the attributes of one graphic mark in one group of graphic marks may be determined by the elastic measurement results corresponding to one region of interest at one time variable value. The shape of the graphic mark may be one of a shape formed by a regular curve such as a rectangular bar, a stereoscopic column, a dot, a line segment, a sector, and a bubble, etc., and may also be a shape formed by an irregular curve, such as shown in FIG. 14. The elastic statistical prompt chart is a statistical chart which shows the correspondence relationship between the elastic measurement results and the statistical variables using the graphic marks above. The statistical chart may generally be based on a three-dimensional Cartesian coordinate system, a two-dimensional Cartesian coordinate system or a polar coordinate system. The graphic marks may also be drawn based on a customized coordinate system.

The attributes of the graphic mark may include shape size, coordinate in the elastic statistical prompt chart and color, etc. The shape size herein may include area or outer dimension, etc. The coordinate in the elastic statistical prompt chart may include the horizontal and vertical coordinates or polar coordinates of the single graphic mark in the elastic statistical prompt chart. The color may represent the color, transparency, contrast or other attributes that are used to render the graphic mark to distinguish them from each other. The magnitude of the value of the elastic measurement result may be shown by the attributes of the graphic mark. For example, the different values of the elastic measurement results may correspond to different shape sizes, different coordinates in the elastic statistical prompt chart and/or different colors.

In one embodiment of the present disclosure, a colored rectangular bar on a two-dimensional coordinate plane may be used to prompt the current measurement result. Each time a tissue elastic measurement result is obtained, a bar may be displayed at the current time on the coordinate plane. The longitudinal height of the bar (i.e. the ordinate in a Cartesian coordinate system) may represent the magnitude of the elasticity result. The data associated with the shape size, the coordinates in the elastic statistical prompt chart and the color, etc. of the graphic mark may determine the value of one of the shape size, the coordinates in the elastic statistical prompt chart and the color of the graphic mark in the elastic statistical prompt chart. The magnitude of the value of the elastic measurement result may determine the magnitude of such data.

In the system of the present embodiment, multiple kinds of graphic mark and corresponding elastic statistical prompt chart may be provided for the user to select. For example, in one embodiment of the present disclosure, a selection instruction about the shape of the graphic mark from the user may be received, and the graphic mark with corresponding shape may be generated according to the selection instruction to generate a corresponding elastic statistical prompt chart. In one embodiment of the present disclosure, the system may set, by default, the graphic mark to be a rectangular bar or a stereoscopic column and the elastic statistical prompt chart to be a column or bar statistical chart. In other embodiments of the present disclosure, various statistical charts in statistics may be used to show the correspondence relationship between the elastic measurement results and the statistical variables.

Figure 5:
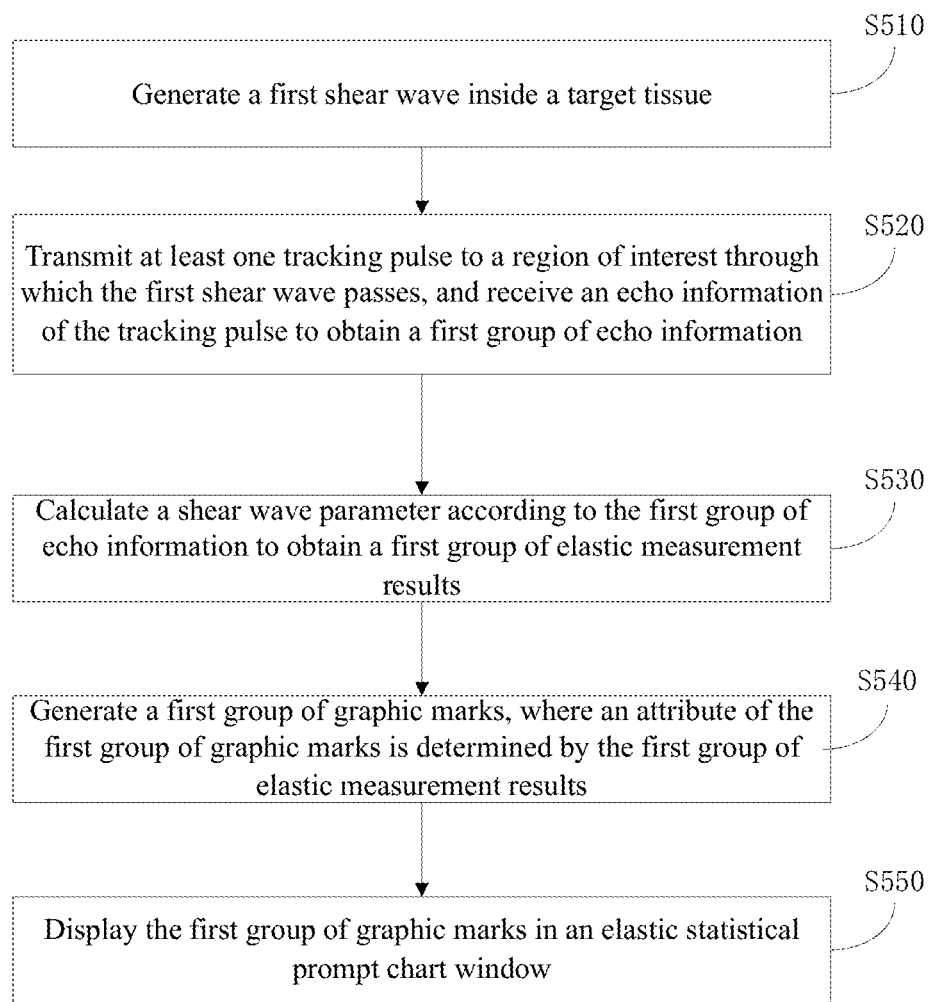
FIG. 5 is a schematic flow chart of one embodiment of an ultrasound elastic measurement display method of the present disclosure

Referring to FIG. 5, an embodiment of the process of generating two adjacent groups of graphic marks is specifically illustrated.

In step 510, a first shear wave may be generated inside the target tissue using the probe;

In step 520, the probe may transmit at least one tracking pulse to the region of interest through which the first shear wave passes, and the receiving circuit and the beam-forming unit may receive the echo information of the tracking pulse to obtain a first group of echo information;

In step 530, the elasticity result calculation unit may calculate the shear wave parameters according to the first group of echo information to obtain a first group of elastic measurement results;

In step 540, the elasticity result calculation unit may generate a first group of graphic marks, where the attributes of the first group of graphic marks are determined by the first group of elastic measurement results;

In step 550, the first group of graphic mark may be displayed in the elastic statistical prompt chart window on the display.

In the embodiment above, a process of generating a group of graphic marks is provided, where one group of graphic marks corresponds to one measurement process of the shear wave. In addition, when performing the second shear wave measurement, the following process will be performed.

Figure 6:
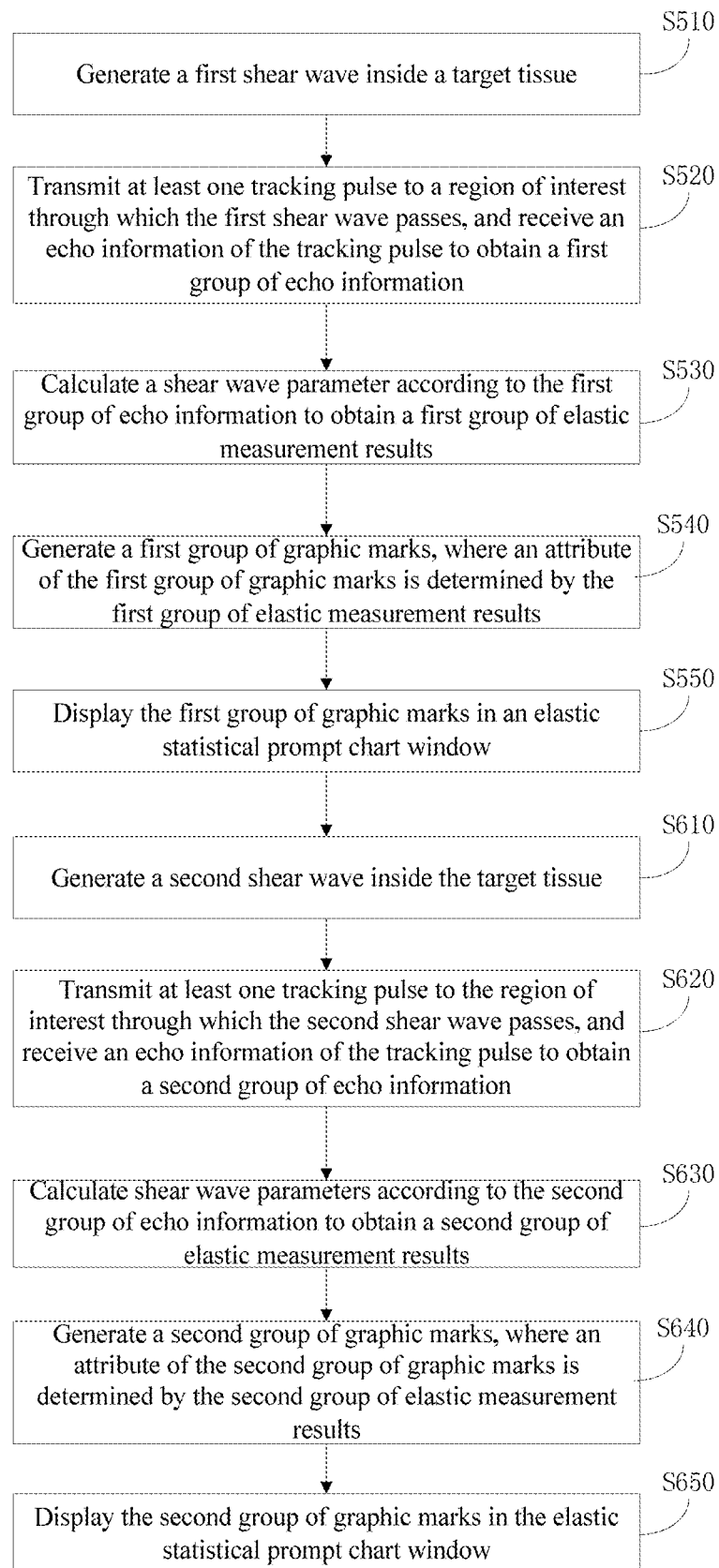
FIG. 6 is a schematic flow chart of the method in another embodiment after the embodiment shown in FIG. 5.

As shown in FIG. 6, after step S550, the method may further include:

In step 610, a second shear wave may be generated inside the target tissue using the probe;

In step 620, the probe may transmit at least one tracking pulse to the region of interest through which the second shear wave passes, and the receiving circuit and the beam-forming unit may receive the echo information of the tracking pulse to obtain a second group of echo information;

In step 630, the elasticity result calculation unit may calculate the shear wave parameters according to the second group of echo information to obtain a second group of elastic measurement results;

In step 640, the elasticity result calculation unit may generate a second group of graphic marks, where the attributes of the second group of graphic marks may be determined by the second group of elastic measurement results;

In step 650, the second group of graphic marks may be displayed in the elastic statistical prompt chart window on the display. In this embodiment, the second group of graphic marks corresponds to the elastic measurement results obtained by the second shear wave measurement.

Regarding the manner for obtaining, and the definition of, the region of interest in the embodiments above, reference may be made to the related description above. In addition, the first group of graphic marks and/or the second group of graphic marks may be the results obtained by the two shear wave measurement processes, and respectively correspond to the shear wave measurement correspondingly performed. Reference may be made to the description above about the graphic marks and it will not be described here again. The processes shown in FIG. 5 and FIG. 6 may also include generating and displaying the ultrasound tissue image, for which the reference may be made to related description above. In addition, the elastic statistical prompt chart window mentioned above may include an area for displaying the elastic statistical prompt chart designated on the display interface or a window area for displaying the elastic statistical prompt chart floating on the display interface.

In step S600, the relationship between the graphic marks and the statistical variables may be displayed on the display to form the elastic statistical prompt chart associated with the region of interest. The image region for displaying part or entire of the elastic statistical prompt chart on the display may be referred to as the elastic statistical prompt chart window.

In the system of this embodiment, different forms of elastic statistical prompt chart may be presented according to required effects.

Figure 7:
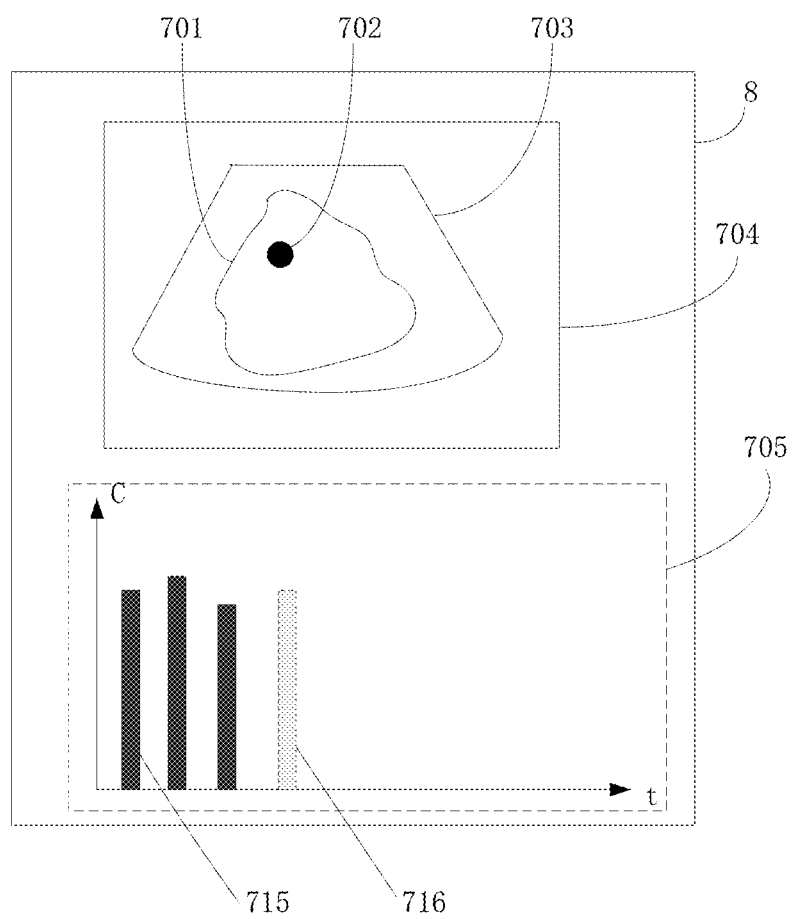
FIG. 7 is a resultant view in the case that there is one region of interest.

For example, as shown in FIG. 7, on the display interface of the display 8, an ultrasound tissue image 703 may be displayed in an ultrasound tissue image display area 704. The ultrasound tissue image display area 704 can be any area on the display interface. The anatomical tissue structure 701 is located on the ultrasound tissue image 703. The ultrasound tissue image herein can be a two-dimensional image or a three-dimensional image. The region of interest 702 may be a region containing a multiple pixels, and the corresponding elastic measurement results thereof may be the statistics in this region, such as an average value, a mean square error, and the like. In this embodiment, the elastic statistical prompt chart may be a histogram statistical chart, and be displayed on the elastic statistical prompt chart window 705. In FIG. 7, the elastic statistical prompt chart window 705 is located outside the ultrasound tissue image display area 704. The multiple groups of graphic marks 715 obtained in the previous few times have been marked as black rectangular bars and have been shown, while the group of graphic mark 716 (shown as a dashed box in FIG. 7) to be obtained next time will be displayed at corresponding location corresponding to the corresponding time variable value. In FIG. 7, the multiple groups of graphic marks may be sequentially displayed according to the order of change of the time variables, and the attributes of one group of graphic marks are determined by the elastic measurement results corresponding to one time variable value. It is also possible to cache the elastic measurement results respectively corresponding to multiple time variable values and generate and display multiple groups of graphic marks at one time. The time variable here may be time-related parameters such as the number of frames of the ultrasound tissue image, the system time, the number of shear wave measurements, and the like. In the embodiment shown in FIG. 6, in the elastic statistical prompt chart window 705, the obtained second group of graphic marks is displayed at the locations adjacent to the first group of graphic marks, thereby achieving sequentially displaying the first and second group of graphic marks according to the order of change of the time variable. When sequentially displaying the first and second group of graphic marks displayed according to the order of change of the time variable, it is also possible that the first group of graphic marks is replaced with the second group of graphic marks according to the order of change of the time variable, thereby achieving the sequential display of the graphic marks by time at the same location.

Figure 8:
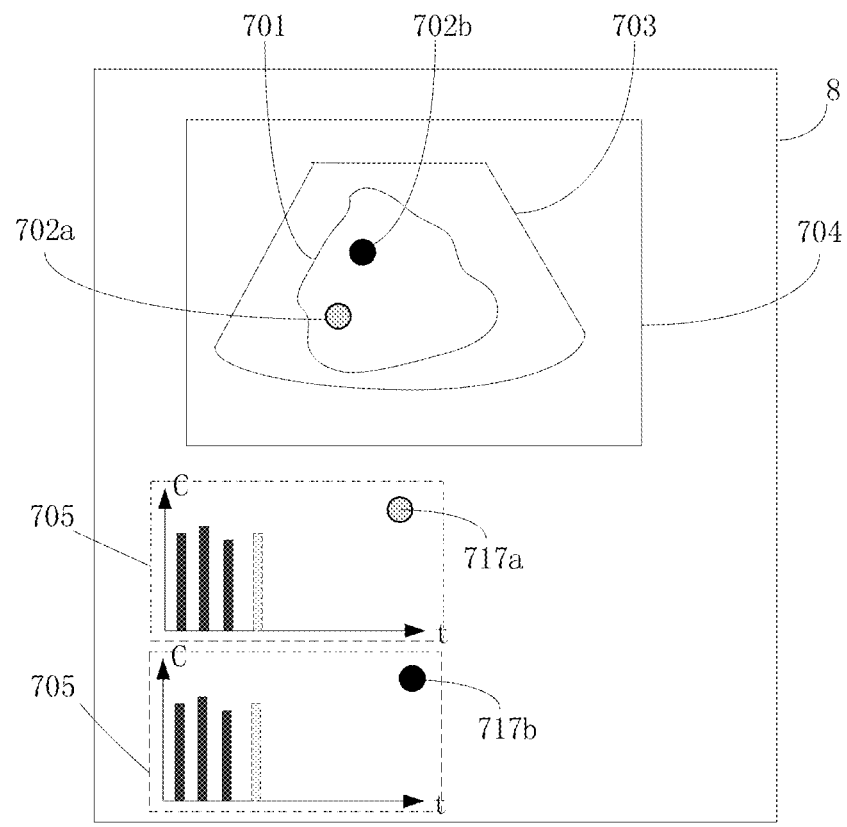
FIG. 8 is a resultant view in the case that there are two regions of interest.
Figure 9:
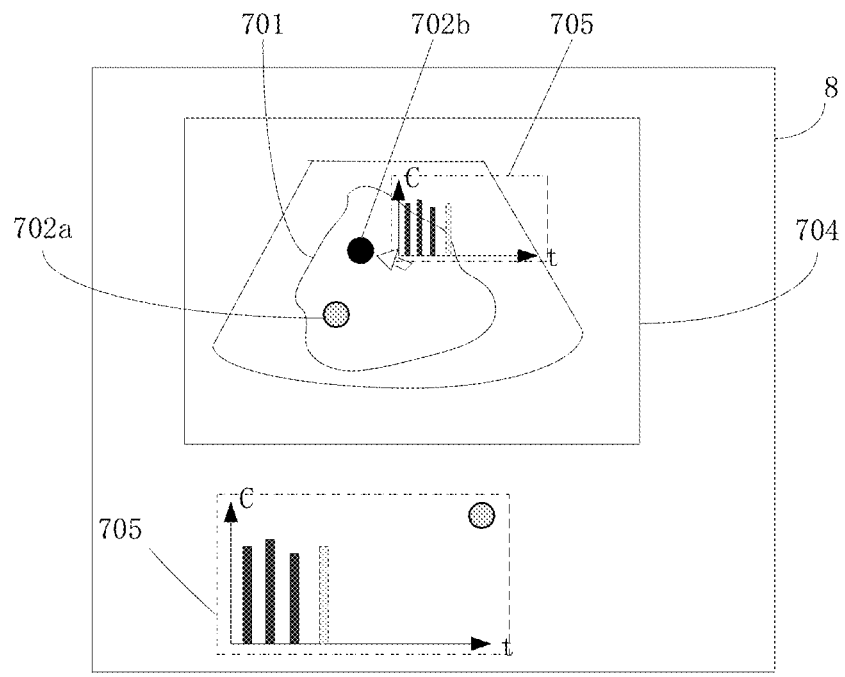
FIG. 9 is a resultant view with a floating window.

Further, as shown in FIG. 8, when there are two or more regions of interest 702a and 702b, a corresponding number of elastic statistical prompt chart windows 705 may be set and used to display the elastic statistics prompt charts corresponding to the regions of interest 702a and 702b. In order to facilitate the user to identify the region of interest corresponding thereto, identifiers 717a and 717b may be displayed on the elastic statistical prompt charts. The elastic statistical prompt chart with the identifier 717a corresponds to the region of interest 702a, and is obtained according to the elastic measurement results of the region of interest 702a. The elastic statistical prompt chart with the identifier 717b corresponds to the region of interest 702b, and is obtained according to the elastic measurement results of the region of interest 702b. The regions of interest 702a and 702b use markers with the same attributes to the identifiers 717a and 717b. Besides the identifier, color may also be used. For example, the elastic statistical prompt chart or the elastic statistical prompt chart window corresponding to the region of interest may use the same color to the region of interest. In FIG. 8, there are two elastic statistical prompt chart windows. In fact, an independent area can be designated directly on the display interface of the display as the elastic statistical prompt chart window for displaying all or selected elastic statistical prompt charts corresponding to multiple regions of interest. In addition, besides being a display area separate from the ultrasound tissue image display area, the elastic statistical prompt chart window may also be a floating window. For example, as shown in FIG. 9, when the real-time position of the cursor is at or near the region of interest 702b, a floating window type elastic statistical prompt chart window 705 may be displayed, and the elastic statistic prompt chart corresponding to the region of interest 702b may be displayed in such elastic statistical prompt chart window 705. As shown in FIG. 9, the floating window type elastic statistical prompt chart window 705 and the separate area-type elastic statistical prompt chart window may be simultaneously displayed on the interface.

In the elastic statistical prompt chart in FIG. 7 to FIG. 9, the Cartesian coordinate system is constructed by using the time variable as the abscissa and using the value of the elastic measurement result as the ordinate to form the elastic statistical prompt chart coordinate system, and then the groups of graphic marks are displayed in this coordinate system to form the elastic statistical prompt chart. Correspondingly, when the measurement method of the elastic measurement result changes, the ordinate of the elastic statistical prompt chart coordinate system will be changed accordingly. Besides the two-dimensional coordinate system, the elastic statistical prompt chart coordinate system may also be a three-dimensional coordinate system. For details, please refer to the following description.

For example, multiple graphic marks may be synchronously displayed on the display according to the spatial positional relationship of the position variables, where the attributes of one graphic mark are determined by the elastic measurement results corresponding to one region of interest. It is also possible to cause the displayed graphic mark to move with the movement of the cursor. For example, when the real-time position of the cursor is located at or close to the region of interest, the graphic marks (or an image mark) corresponding to the current region of interest may be displayed.

Figure 10:
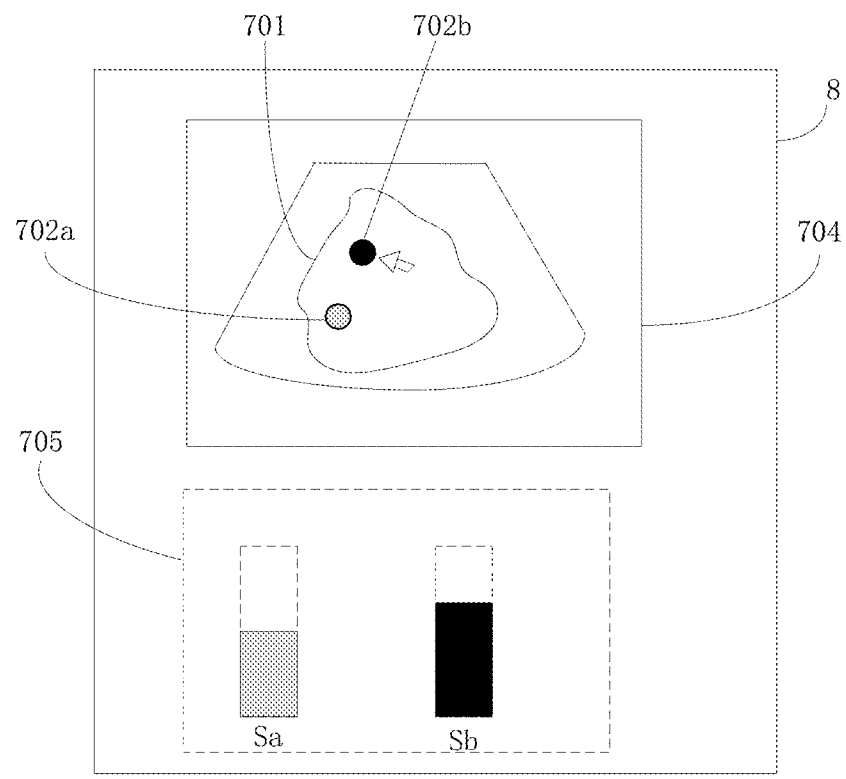
FIG. 10 is a resultant view in the case that there are multiple regions of interest.
Figure 11:
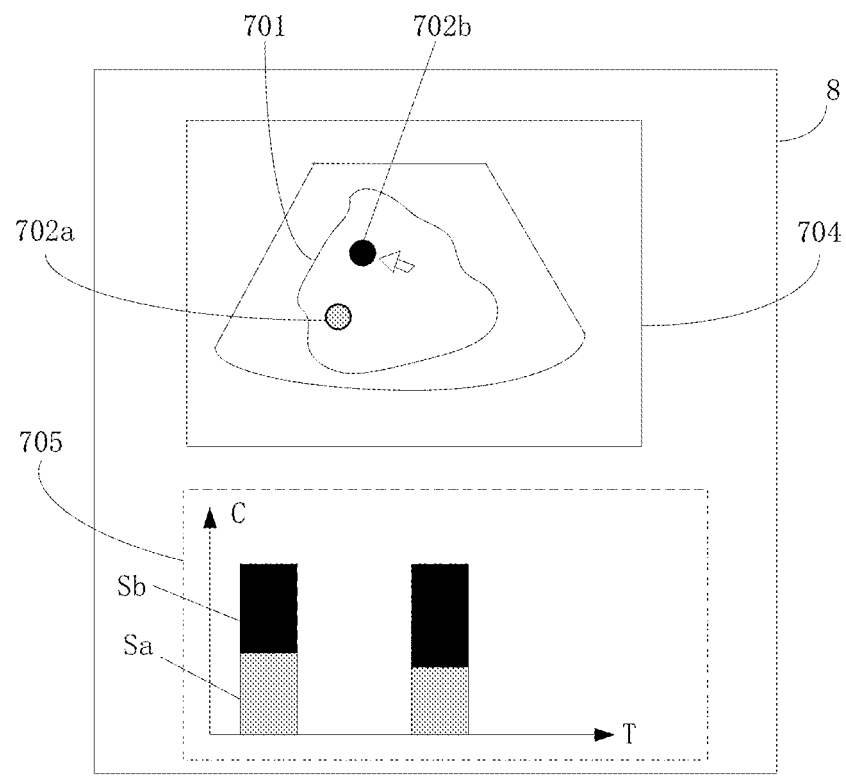
FIG. 11 is a resultant view in the case that there are multiple regions of interest.

As shown in FIG. 10, there are two regions of interest 702a and 702b on the display interface, and the elastic statistic prompt charts corresponding to the regions of interest 702a and 702b are displayed in the elastic statistical prompt chart window 705 that is separate from the ultrasound tissue image display region. In the present embodiment, the elastic statistical prompt chart may be variable rectangular bars Sa and Sb. Of course, a stereoscopic rectangular column, a colored rectangular bar or a stereoscopic column, etc. may also be used. In order to distinguish the correspondence relationships between the rectangular bars and the regions of interest 702a and 702b, the rectangular bars Sa and Sb may be marked with the same color as the regions of interest 702a and 702b, and alternatively, the rectangular bars Sa and Sb may be marked with the same text prompt information as the region of interest 702a and 702b, and alternatively, the rectangular bars Sa and Sb corresponding to the regions of interest 702a and 702b may be displayed according to the spatial positional relationship of the position variables. As shown in FIG. 10, in the ultrasound tissue image, the region of interest 702a is on the left side of the region of interest 702b, and therefore in the elastic statistics prompt chart window 705, the rectangular bar Sa is on the left side of the rectangular bar Sb. Alternatively, as shown in FIG. 11, in the ultrasound tissue image, the region of interest 702a is below the region of interest 702b, and therefore in the elastic statistical prompt chart window 705, the rectangular bar Sa is below the rectangular bar Sb. In FIG. 10, the multiple groups of graphic marks obtained according to the time variable are displayed at the original display position by replacement. For example, based on the method shown in FIG. 6 and the display effect shown in FIG. 10, the first group of graphic marks is displayed as rectangular bars Sa and Sb filled with colors in the elastic statistical prompt chart window 705, and the second group of graphic marks replaces the first group of graphical display markers at the display position of the first group of graphic marks, that is, when displaying the second group of graphic marks in the elastic statistic prompt chart window 705, the rectangular bars Sa and Sb will be displayed at the locations indicated by the dashed boxes. Both the first group of graphic marks and the second group of graphic marks may also be displayed in the same elastic statistical prompt chart coordinate system. For example, the multiple groups of graphic marks corresponding to each region of interest may be displayed in different areas, as shown in FIG. 8 and FIG. 9. Alternatively, as shown in FIG. 11, an elastic statistical prompt chart coordinate system using the time variable as the abscissa axis and the elastic measurement result C as the ordinate axis is constructed, and the obtained multiple groups of graphic marks are sequentially displayed according to the time variable. When displaying each group of graphic marks, the multiple graphic marks corresponding to the multiple regions of interest are synchronously displayed. As shown in FIG. 11, the rectangular bars Sa and Sb corresponding to the regions of interest 702a and 702b are displayed by superimposition. Further, when displaying by superimposition, the superposition may also be performed according to the spatial positional relationship of the region of interest. When the measurement manner of the elastic measurement result C is changed by the user selection, the ordinate unit of the elasticity statistical prompt chart coordinate system may also be changed.

Figure 12:
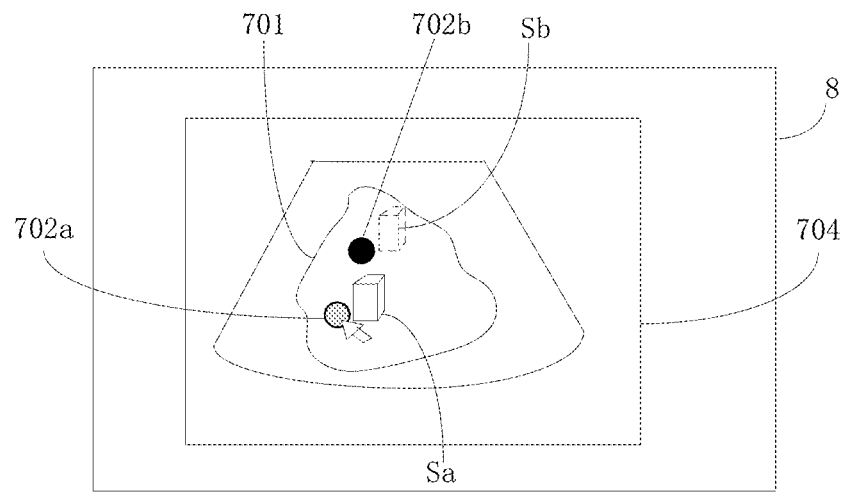
FIG. 12 is a resultant view with graphic marks superimposed on the ultrasound image in the case that there are multiple regions of interest.

The elastic statistical prompt chart window may also be a floating window. The elastic statistical prompt chart window 705 shown in FIG. 11 may also adopt the floating window shown in FIG. 9. Alternatively, the rectangular bars Sa and Sb in FIG. 10 may also be floating. As shown in FIG. 12, the ultrasound tissue image may be used as an elastic statistical prompt chart coordinate system. When real-time position of the cursor is located at or near the region of interest, a rectangular bar corresponding to the region of interest is displayed. In another embodiment, as shown in FIG. 12, the rectangular bars Sa and Sb may also be displayed directly at the image display position of the region of interest on the ultrasound tissue image. The rectangular bar here may also be a graphic mark with a shape of stereoscopic column.

In another example, the two cases above may be combined. The graphic marks may be displayed on the display according to the order of change of the time variable and the spatial positional relationship of the position variable may simultaneously be shown. For example, when the real-time position of the cursor is located at or close to the region of interest, the multiple groups of graphic marks corresponding to the current region of interest may be sequentially displayed according to the order of change of the time variable. Alternatively, the multiple groups of graphic marks may be sequentially displayed on the display according to the order of change of the time variables and at the same time the multiple graphic marks in each group of the graphic marks may be synchronously displayed according to the spatial positional relationship of the position variables, where the attributes of one graphic mark in one group of graphic marks is determined by the elastic measurement results corresponding to one region of interest at one time variable value. Specifically, as shown in FIG. 10, FIG. 11, FIG. 9, and FIG. 8, the correspondence relationship between the elastic measurement results of multiple regions of interest and the time variable and the position variable may be simultaneously displayed.

Figure 13:
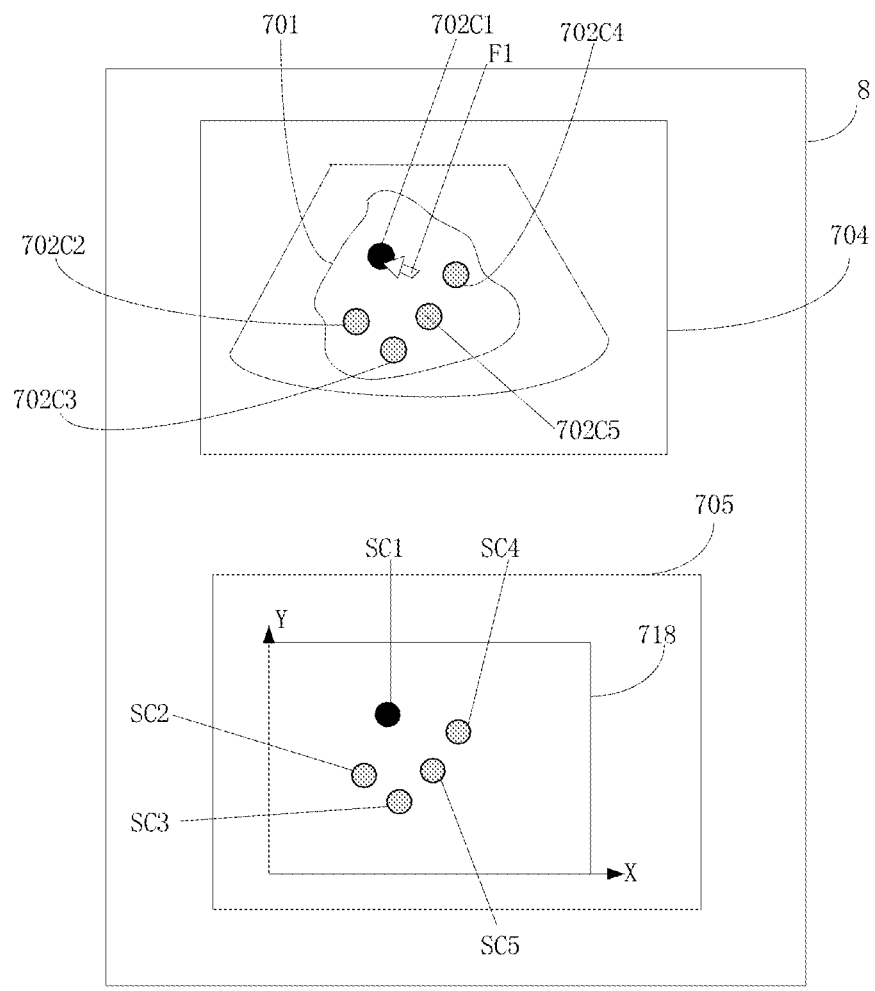
FIG. 13 is a resultant view with separate elastic statistical prompt chart window in the case that there are multiple regions of interest.

In the embodiments above, it can be seen that, besides being located outside of the ultrasound tissue image display area, the elastic statistical prompt chart may be a floating window. Alternatively, as shown in FIG. 12, the elastic measurement results represented by the graphic marks may be displayed directly on the ultrasound tissue image. For example, the graphic marks corresponding to the region of interest may be displayed at the image display position of said region of interest. When there are multiple regions of interest, multiple graphic marks may be respectively displayed at the image display positions of the multiple regions of interest. Further, in addition to the methods above, in one embodiments of the present disclosure, a display method may further be provided, as shown in FIG. 13. On the display interface of the display 8, the ultrasound tissue image is displayed in the ultrasound tissue image display area 704. The ultrasound tissue image display area 704 may be any area on the display interface. The anatomical tissue structure 701 is located on the ultrasound tissue image, and multiple regions of interest 702C1, 702C2, 702C3, 702C4, 702C5 are disposed in the anatomical tissue structure 701. In the elastic statistical prompt chart window 705 separate from the ultrasound tissue image display area 704, the elastic statistical prompt chart coordinate system is constructed with the position variable as the coordinate axis. In the coordinate system, the horizontal and vertical coordinates are the coordinates of the pixels on the ultrasound tissue image. The maximum range of ultrasound tissue image regions exhibited by the coordinate system includes multiple regions of interest 702C1, 702C2, 702C3, 702C4, 702C5. The graphic marks (SC1, SC2, SC3, SC4, SC5) corresponding to the image positions of the regions of interest are marked in the coordinate system according to the spatial positional relationship of the multiple regions of interest 702C1, 702C2, 702C3, 702C4, 702C5. Thus, by means of indirect display, the elastic tissue distribution in the ultrasound tissue image area to be observed is shown. The position of the cursor F1 may be identified. When the cursor F1 is moved to the corresponding region of interest (e.g., 702C1) in the ultrasound tissue image, the graphic mark SC1 corresponding to the region of interest 702C1 is highlighted in the elastic statistical prompt chart window 705 (e.g., it is highlighted as black in FIG. 13). The positional variable (e.g., the coordinate position relationship of the multiple regions of interest in the ultrasound tissue image in FIG. 13) is used to establish the elastic statistical prompt chart coordinate system, and then the multiple graphic marks are respectively displayed in the elastic statistical prompt chart coordinate system at the positions corresponding to the image display positions of the corresponding regions of interest, thereby achieving mapping the position of the region of interest in the ultrasound tissue image and the elastic measurement results in the elastic statistic prompt chart according to the spatial positional relationship of the position variable to synchronously display the multiple graphic marks corresponding to the multiple regions of interest. In addition, when there are consecutive multiple measurements, the graphic marks in FIG. 13 (the circles shown in the figure) will be replaced with the latest measured elastic measurement results according to the order of change of the time variables. For example, the multiple graphic marks corresponding to the multiple regions of interest in the first group of graphic marks are displayed according to the display manner of FIG. 13. When the second group of graphic marks is obtained, the data in the elastic statistical prompt chart window 705 may be updated with the multiple graphic marks corresponding to the multiple regions of interest in the second group of graphic marks.

The modification of the embodiment shown in FIG. 13 is as shown in FIG. 14. The form of the elastic statistical prompt chart coordinate system may not be limited to a rectangular or a form of strict coordinate system, but may also be a circular or annular. Moreover, the graphic marks displayed in the elastic statistical prompt chart coordinate system may not be limited to dot, circular block, stereoscopic column, rectangular bar, or the like, but may also be an area surrounded by an irregular curve shown in FIG. 14. Of course, the areas in FIG. 14 may also be surrounded by regular curves. The areas formed by the irregular curves or the regular curves correspond to, in a spatial positional relationship, the coordinate positions of the multiple regions of interest in the ultrasound tissue image. Similarly, the areas formed by the irregular curves or the regular curves are presented as graphic marks SC1', SC2', SC3', SC4', SC5' which respectively correspond to the multiple regions of interest 702C1, 702C2, 702C3, 702C4, 702C5. The values of the elastic measurement results corresponding to the multiple regions of interest 702C1, 702C2, 702C3, 702C4, and 702C5 determine the attribute parameters such as shape size and/or color, etc. of the areas formed by the irregular curves or the rule curves (graphic marks SC1', SC2', SC3', SC4', SC5'), such that the user can more intuitively understand the tissue elastic distribution of the ultrasound tissue image region containing the multiple regions of interest. The multiple regions of interest 702C1, 702C2, 702C3, 702C4 and 702C5 may be selected by the user, or be multiple regions or multiple pixels obtained by automatically discretely segmenting the image in a certain range by the system. Further, in some embodiments, the boundary coordinates of the areas SC1', SC2', SC3', SC4', SC5' formed by the irregular curves or the regular curves may be corresponded to the boundary coordinates of the areas covered by the multiple regions of interest 702C1, 702C2 702C3, 702C4 and 702C5 in the ultrasound tissue image.

In addition, the position of the cursor F1 may be identified on the displayed ultrasound tissue image, and when the position of the cursor is at or near the region of interest, the graphic mark corresponding to this region of interest may be highlighted in the elastic statistical prompt chart. For example, in FIG. 13, the graphic mark SC1 corresponding to the region of interest 702C1 is highlighted by filling with black. In FIG. 14, the boundary of the area SC1' formed by the irregular curve is highlighted.

In one embodiment, the probe may be used to transmit ultrasound beams to the target tissue to obtain the ultrasound tissue image of the target tissue. The ultrasound tissue image may be displayed and the region of interest may be marked. It is also possible to display the ultrasound tissue image and mark the position at which the shear wave is generated so as to show the position of the region of interest and/or the position at which the shear wave is generated to the user.

In one embodiment, a certain area may be designated on the display interface of the display for displaying the elastic statistical prompt chart, and the elastic statistical prompt chart may be located outside the ultrasound tissue image display area. Alternatively, when the position of the cursor is at or near the region of interest, the elastic statistical prompt chart may be displayed near the position of the cursor, thereby achieving the effect of the elastic statistical prompt chart following the cursor.

Figure 15:
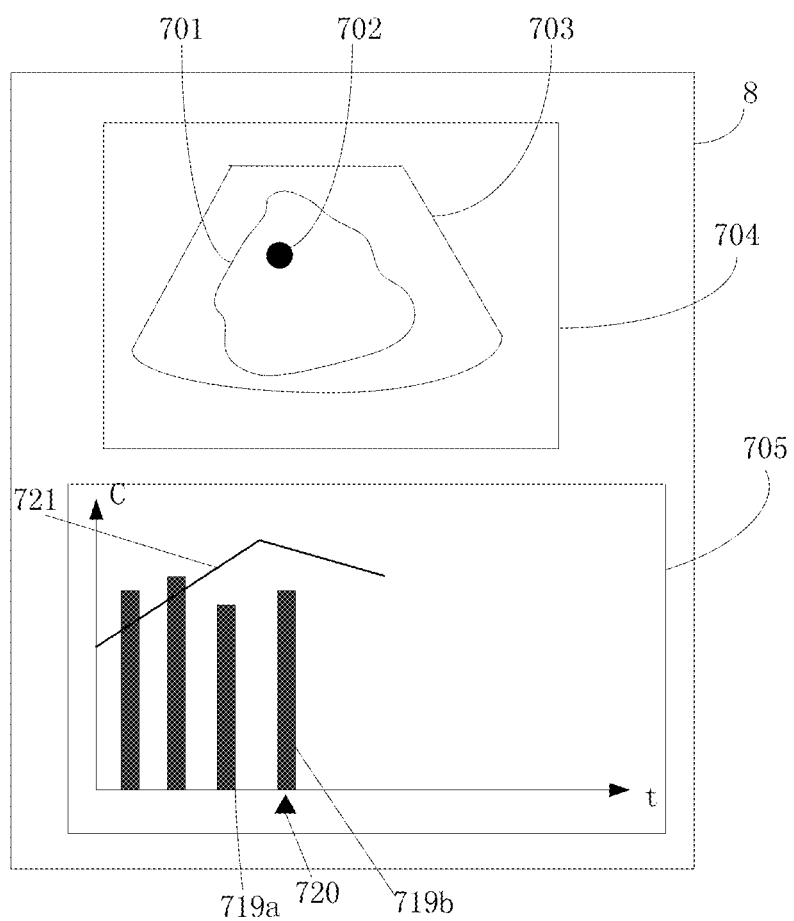
FIG. 15 is a resultant view in the case that there is one region of interest.

In one embodiment, the step S600 may further include highlighting the currently displayed graphic marks in the elastic statistical prompt chart. For example, in the embodiment shown in FIG. 5, the method may further include highlighting the first group of graphic marks or displaying the highlighted marks indicating the first group of graphic marks. Highlighting may be implemented by deepening the color, micro-enlargement, filling with color, improving the brightness and other rendering processing methods. Alternatively, as shown in FIG. 15, a highlight mark 720 (shown as a triangle in the figure) may be display on the first group of graphic marks 719*a* or the second group of graphic marks 719*b* obtained by two adjacent measurements. When displaying the second group of graphic marks 719*b*, the triangular highlight mark 720 may be displayed below the second group of graphic marks 719*b* to highlight the currently displayed graphic marks.

In addition, the system of the present embodiment may further provide a function of data playback and secondary statistics which can be performed by the user autonomously. For example, in one embodiment of the present disclosure, after step S600, the method may further include:

First, the graphic marks selected by the user on the elastic statistical prompt chart may be obtained. Thereafter, the elastic measurement results respectively corresponding to the selected graphic marks may be obtained, and statistically analyzed to obtain statistical evaluation value. The statistical evaluation value may be displayed. The statistical evaluation value herein may be obtained by any one or two or more statistical analysis operations of averaging, finding the maximum, finding the minimum, and calculating the standard deviation, etc. performed on the elastic measurement results respectively corresponding to the selected graphic marks. Therefore, the statistical evaluation value may include at least one of average, maximum, minimum, and standard deviation, etc. In the embodiment shown in FIG. 6, such selection may also be used for the function of secondary playback statistics, and the selected graphic marks may include a part or all of the first and second group of graphic marks. The selected graphic marks may be either a part or all of the multiple groups of graphic marks obtained based on the time variable or a part or all of the multiple graphic marks obtained based on the position variable. That is, the statistical evaluation value may be a secondary statistical analysis result based on the elastic measurement results in a time period, or be a secondary statistical analysis result based on the elastic measurement results in a certain ultrasound tissue image region.

In addition, text prompt information related to the statistics of the elastic measurements may further be displayed on the display. The statistic here may include the statistical evaluation value obtained by the secondary playback statistic function mentioned above or the statistic of the parameters in the region of interest calculated in step S300 above. For example, when the currently displayed graphic mark is highlighted in the elastic statistical prompt chart, the text prompt information identifier may correspondingly display the elastic measurement results corresponding to the currently displayed graphic mark, e.g., display the statistics of the parameters in the region of interest corresponding to the currently displayed graphic mark.

When performing the secondary statistical function, the graphic marks selected by the user on the elastic statistical prompt chart may be highlighted in the elastic statistical prompt chart. After an acquisition in a time period is completed, the system may perform automatic statistical calculation on the part of the results selected by the user, and display the final calculation result. The selected bar may be specially marked for user identification, such as changing its color.

For the elastic statistical prompt chart, the system of the present embodiment provides multiple functional operations to the user. For example, the coordinates of the elastic statistical prompt chart, the attribute representation of the graphic marking and the like can be changed. In one embodiment of the present disclosure, an update instruction for the user to change the ordinate range may be obtained in the elastic statistical prompt chart. The elastic statistical prompt chart may be updated based on the update instruction. It is convenient for user to change the presentation form of the elastic statistical prompt chart according to the needs of his own. In one embodiment of the present disclosure, an update instruction for the user to change the shape attribute of the graphic mark may be obtained in the elasticity statistical prompt chart, and the shape of the graphic mark in the elasticity statistical prompt chart may be updated based on the update instruction.

Furthermore, color-coded information may also be displayed in the elastic statistical prompt chart, where the change in the value of the elastic measurement result may be represented by the color coding level. As mentioned before, the graphic marks may also display the changes in the value of the elastic measurement results by changing the color attribute.

In one embodiment of the present disclosure, the step of displaying the elastic statistical prompt chart may further include:

calculating an average value of the elastic measurement results respectively corresponding to the selected graphic marks, or obtaining an elastic reference value related to the region of interest. In this embodiment, the elastic reference value may be a normal value obtained based on experience according to the characteristics of a certain anatomical structure itself;

displaying a curve representing the average value or the elastic reference value in the elastic statistical prompt chart (such as the polyline 721 shown in FIG. 15). In this way, the elastic results measured in real-time can be compared with the normal value or the average value, thereby providing more reference for the user.

In one embodiment, in the elastic statistical prompt chart, the graphs representing the elastic measurement results that are higher or lower than the curve may be highlighted. For example, in the embodiment shown in FIG. 6, the relationship between the first group of elastic measurement results or the second group of elastic measurement results and a standard value may be determined, where the standard value may include the elastic reference value mentioned above or the statistical evaluation value of the elastic measurement results corresponding respectively to the graphic marks selected by the user. When the first group of elastic measurement results or the second group of elastic measurement results is higher or lower than the standard value, the first group of graphic marks or the second group of graphic marks may be highlighted. The highlighting or rendering mentioned herein is intended to distinguish the graphic marks from other unmarked graphic marks. Therefore, besides the highlighting or rendering methods mentioned above, other rendering or highlighting methods may also be used.

A person skilled in the art can understand that all or part of the processes for implementing the methods in the embodiments above can be implemented by a computer program instructing related hardware. The program can be stored in a computer readable storage medium. When executed, the program can implement the processes in the embodiments of the methods described above. The storage medium may be a magnetic disk, an optical disk, a read-only memory (ROM), or a random access memory (RAM), etc.

The steps of the methods in the embodiments above are not limited to the manners described in the embodiments above. Without violating the logic in the context, the steps will not be performed strictly in the direction indicated by the arrows in the drawings, but can be interleaved, replaced or interchanged with each other, which will not affect the implementation of the solution of the present disclosure.

The above is a detailed description of the present disclosure in connection with the specific embodiments. However, it cannot be interpreted as that the specific implement of the present disclosure is limited to the description. For those skilled in the art to which the present disclosure pertains, a number of simple deductions or substitutions can be made without departing from the concept of the present disclosure, which should all fall in the protection scope of the present disclosure.

The invention claimed is:

1. An elastic ultrasonic measurement display method, comprising:

transmitting ultrasound beams into a target tissue;
generating an ultrasound image from ultrasound echoes received from the target tissue;
displaying the ultrasound image in a first area of a display;
generating a first shear wave inside a target tissue which passes through a first region of interest;
transmitting a first tracking pulse to the first region of interest through which the first shear wave passes;
receiving an echo information of the first tracking pulse;
calculating a first shear wave parameter according to the echo information of the first tracking pulse to obtain a first elastic measurement result corresponding to the first region of interest;
generating a first graphic mark,
wherein an attribute of the first graphic mark is determined by the first elastic measurement result;
displaying the first graphic mark in a first elastic statistical prompt chart associated with the first region of interest,
wherein a location of the first graphic mark in the first elastic statistical prompt chart corresponds to a first statistical variable,
wherein the first elastic statistical prompt chart is displayed in a second area of the display simultaneously with the ultrasound image in the first area;
generating a second shear wave inside the target tissue which passes through a second region of interest;
transmitting a second tracking pulse to the second region of interest through which the second shear wave passes;
receiving an echo information of the second tracking pulse;
calculating a second shear wave parameter according to the echo information of the second tracking pulse to obtain a second elastic measurement result corresponding to the second region of interest;
obtaining a correspondence relationship between the second elastic measurement result corresponding to the second region of interest and a second statistical variable;
generating an additional graphic mark, wherein an attribute of the additional graphic mark is determined by the second elastic measurement result corresponding to the second region of interest; and
displaying the additional graphic mark in a second elastic statistical prompt chart associated with the second region of interest,
wherein a location of the additional graphic mark in the second elastic statistical prompt chart corresponds to the second statistical variable,
wherein the second elastic statistical prompt chart is displayed in a third area of the display simultaneously with the first elastic statistical prompt chart in the second area and the ultrasound image in the first area.

2. The elastic ultrasonic measurement display method according to claim 1, wherein each of the first statistical variable and the second statistical variable comprises at least one of a position variable and a time variable.

3. The elastic ultrasonic measurement display method according to claim 2, wherein, the position variable changes in a propagation direction of the first shear wave, a propagation direction of the second shear wave, or in a propagation direction of ultrasound beams or tracking beams.

4. The elastic ultrasonic measurement display method according to claim 1, wherein the attribute of the first graphic mark comprises at least one of: a shape of the first graphic mark, a size of the first graphic mark, a coordinate of the first graphic mark in the first elastic statistical prompt chart, and a color of the first graphic mark.

5. The elastic ultrasonic measurement display method according to claim 1, wherein, each of the first statistical variable and the second statistical variable comprises a time variable, and generating the first graphic mark and the additional graphic mark comprises: generating multiple groups of graphic marks, wherein an attribute of one of the multiple groups of graphic marks is determined by an elastic measurement result corresponding to a value of the time variable.

6. The elastic ultrasonic measurement display method according to claim 5, wherein displaying the first graphic mark in the first elastic statistical prompt chart comprises: displaying sequentially multiple groups of graphic marks on the display according to an order of change of time variable; displaying the first graphic mark corresponding to a selected region of interest on the display when a position of a cursor is at or near the selected region of interest; or displaying the multiple groups of graphic marks respectively at image display positions of multiple regions of interest.

7. The elastic ultrasonic measurement display method according to claim 1, further comprising:
   transmitting the ultrasound beams into the target tissue by a probe to obtain the ultrasound tissue image of the target tissue;
   displaying the ultrasound tissue image; and
   marking the first region of interest and/or a position at which the first shear wave is generated on the ultrasound tissue image.

8. The elastic ultrasonic measurement display method according to claim 1, wherein each of the first elastic measurement result or the second elastic measurement result is represented by one of Young's modulus, shear modulus, shear wave velocity and shear wave propagation distance.

9. The elastic ultrasonic measurement display method according to claim 1, further comprising:
   obtaining graphic marks selected by a user on the first elastic statistical prompt chart;
   obtaining elastic measurement results respectively corresponding to the selected graphic marks;
   obtaining a statistical evaluation value by performing a statistical analysis on the obtained elastic measurement results; and
   displaying the statistical evaluation value.

10. The elastic ultrasonic measurement display method according to claim 9, further comprising: highlighting, in the first elastic statistical prompt chart, the first graphic marks selected by the user in the first elastic statistical prompt chart.

11. The elastic ultrasonic measurement display method according to claim 10, further comprising:
   highlighting a first group of graphic marks or a second group of graphic marks when a first group of elastic measurement results or a second group of elastic measurement results is higher or lower than a standard value.

12. The elastic ultrasonic measurement display method according to claim 1, further comprising:
   obtaining a standard value; and
   displaying a curve representing the standard value in the first elastic statistical prompt chart.

13. The elastic ultrasonic measurement display method according to claim 1, further comprising:
   determining a position of a cursor in the ultrasound tissue image, and when the position of the cursor is at or close to the first region of interest, highlighting the first graphic mark corresponding to the first region of interest in the elastic statistical prompt chart.

14. The elastic ultrasonic measurement display method of claim 1, wherein the first region of interest is marked within the ultrasound image using a first marker, the second region of interest is marked within the ultrasound image using a second marker, the first elastic statistical prompt chart is associated with the first region of interest using a first identifier and the second elastic statistical prompt chart is associated with the second region of interest using a second identifier.

15. The elastic ultrasonic measurement display method of claim 14, wherein the first and second identifiers are respectively associated with the first and second markers by color.

16. The elastic ultrasonic measurement display method according to claim 1, wherein the attribute of the additional graphic mark comprises at least one of: a shape of the additional graphic mark, a size of the additional graphic mark, a coordinate of the additional graphic mark in the second elastic statistical prompt chart, and a color of the additional graphic mark.

* * * * *